(12) United States Patent
Splawski et al.

(10) Patent No.: US 6,342,357 B1
(45) Date of Patent: Jan. 29, 2002

(54) ALTERATIONS IN THE LONG QT SYNDROME GENES KVLQT1 AND SCN5A AND METHODS FOR DETECTING SAME

(75) Inventors: Igor Splawski, Alston; Mark T. Keating, Brookline, both of MA (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/634,920

(22) Filed: Aug. 9, 2000

Related U.S. Application Data
(60) Provisional application No. 60/190,057, filed on Mar. 17, 2000, and provisional application No. 60/147,488, filed on Aug. 9, 1999.

(51) Int. Cl.[7] .......................... C12Q 1/68; C12P 19/34; C07H 21/04
(52) U.S. Cl. .......................... 435/6; 435/91.1; 435/91.2; 536/23.1; 536/24.3
(58) Field of Search .......................... 435/6, 91.1, 91.2; 536/23.1, 24.3

(56) References Cited

U.S. PATENT DOCUMENTS
5,599,673 A   2/1997   Keating et al.

FOREIGN PATENT DOCUMENTS
WO   WO 97/23598   7/1997

OTHER PUBLICATIONS
Franqueza et al., JBC, Jul. 23, 1999, vol. 274, abstract only.*
Abriel, H. et al., Circulation 102(8):921–925, 2000.
Al Rakaf, M. et al., Int'l. J. of Pediatric Otorhinolaryngology 39:163–168, 1997.
Benhorin, J. et al., Hum. Mutat. 12(1):72, 1998.
Iwasa, H. et al., J. Hum. Genet. 45(3):182–183, 2000.
Jongbloed, R.J. et al., Hum. Mutat. 13(4):301–310, 1999.
Kanters, J.K. et al., J. Cardiovasc. Electrophysiol. 9(6):620–624, 1998.
Kubota, T. et al., J. Cardiovasc. Electrophysiol. 11(9):1048–1054, 2000.
Larsen, L.A. et al., Eur. J. Hum. Genet. 7(6):724–728, 1999.
Napolitano, C. et al., J. Cardiovasc. Electrophysiol 11(6):691–696, 2000.
Saarinen, K. et al., Hum. Mutat. 11(2):158–165, 1998.
Wang, Z. et al., J. Cardiovasc. Electrophysiol. 10(6):817–826, 1999.
Wei, J. et al., Hum. Mutat. 15(4):387–388, 2000.
Yamagishi, H. et al., Hum. Mutat. 11(6):481, 1998.
Ackerman, M.J. "The Long QT Syndrome: Ion Channel Diseases of the Heart", Mayo Clin. Proc., 1998; 73:250–269.
Ackerman, M.J. et al. "Molecular Diagnosis of the Inherited Long–QT Syndrome in a Woman Who Died After Near–Drowning", N. Engl. J. Med., Oct. 7, 1999; 341(15):1121–1125.

(List continued on next page.)

Primary Examiner—W. Gary Jones
Assistant Examiner—Jehanne Souaya
(74) Attorney, Agent, or Firm—Rothwell, Figg, Ernst & Manbeck, P.C.

(57) ABSTRACT

Long QT Syndrome (LQTS) is a cardiovascular disorder characterized by prolongation of the QT interval on electrocardiogram and presence of syncope, seizures and sudden death. Five genes have been implicated in Romano-Ward syndrome, the autosomal dominant form of LQTS. These genes are KVLQT1, HERG, SCN5A, KCNE1 and KCNE2. Mutations in KVLQT1 and KCNE1 also cause the Jervell and Lange-Nielsen syndrome, a form of LQTS associated with deafness, a phenotypic abnormality inherited in an autosomal recessive fashion. Mutational analyses were used to screen 262 unrelated individuals with LQTS for mutations in the five defined genes. A total of 134 mutations were observed of which eighty were novel.

17 Claims, 5 Drawing Sheets

OTHER PUBLICATIONS

Ackerman, M.J. et al. "A Novel Mutation in KVLQT1 is the Molecular Basis of Inherited Long QT Syndrome in a Near–Drowing Patient's Family", *Pediatr. Research*, 1998; 44(2):148–153.

Akai, J. et al. "A novel SCN5A mutation associated with idiopathic ventricular fibrillation without typical ECG findings of Brugada syndrome", *FEBS*, 2000; 479:29–34.

An, R.H. et al. "Novel LQT–3 Mutation Affects $Na^+$ Channel Activity Through Interactions Between $\alpha$–and $\beta_1$–Subunits", *Circ. Res.*, 1998; 83:141–146.

Baroudi, G. et al. "SCN5A mutation (T1620M) causing Brugada syndrome exhibits different phenotypes when expressed in *Xenopus oocytes* and mammalian cells", *FEBS*, 2000; 467:12–16.

Benhorin, J. et al. "Effects of Flecainide in Patients with New SCN5A Mutation. Mutation–Specific Therapy for Long–QT Syndrome?", *Circulation*, 2000; 101:1698–1706.

Benhorin, J. et al. "Evidence of Genetic Heterogeneity in the Long QT Syndrome", *Science*, Jun. 25, 1993; 260:1960–1962.

Bennett, P.B. et al. "Molecular mechanism for an inherited cardiac arrhythmia", *Nature*, Aug. 24, 1995; 376:683–685.

Bezzina, C. et al. "A Single $Na^+$ Channel Mutation Causing Both Long–QT and Brugada Syndromes", *Circ. Res.*, 1999; 85:1206–1213.

Bulman, D.E. "Phenotype variation and newcomers in ion channel disorders", *Human Molecular Genetics*, 1997; 6(10):1679–1685.

Chen, Q. et al. "Genetic basis and molecular mechanism for idiopathic ventricular fibrillation", *Nature*, Mar. 19, 1998; 392:293–296.

Chen, Q. et al. "Homozygous Deletion in KVLQT1 Associated with Jervell and Lange–Nielsen Syndrome", *Circulation*, 1999; 99:1344–1347.

Chouabe, C. et al. "Novel mutations in KvLQT1 that affect $I_{ks}$ activation through interactions with Isk", *Cardiovascular Research*, 2000; 45:971–980.

Chouabe, C. et al. "Properties of KvLQT1 $K^+$ channel mutations in Romano–Ward and Jervell and Lange–Nielsen inherited cardiac arrhythmias", *The EMBO Journal*, 1997; 16(17):5472–5479.

Clancy, C.E. et al. "Linking a genetic defect to its cellular phenotype in a cardiac arrhythmia", *Nature*, Aug. 5, 1999; 400:566–569.

Coonar, A.S. et al. "Molecular Genetics of Familial Cardiomyopathies", *Advances in Genetics*, 1997; 35:285–324.

Curran, M. et al. "Locus Heterogeneity of Autosomal Dominant Long QT Syndrome", *J. Clin. Invest.*, 1993; 92:799–803.

De Jager, T. et al. "Evidence of a long QT founder gene with varying phenotypic expression in South African families",*J. Med. Genet.*, 1996; 33:567–573.

Deschenes, I. et al. "Electrophysiological characterization of SCN5A mutations causing long QT (E1784K) and Brugada (R1512W and R1432G) syndromes", *Cardiovascular Research*, 2000; 46:55–65.

Donger, C. et al. "KVLQT1 C–Terminal Missence Mutation Causes a Forme Fruste Long–QT Syndrome", *Circulation*, 1997; 96:2778–2781.

Dumaine, R. et al. "Ionic Mechanisms Responsible for the Electrocardiographic Phenotype of the Brugada Syndrome Are Temperature Dependent", *Circ. Res.*, 1999; 85:803–809.

Franqueza, L. et al. "Long QT Syndrome–associated Mutations in the S4–S5 Linker of KvLQT1 Potassium Channels Modify Gating and Interaction with minK Subunits", *J. Biological Chemistry*, Jul. 23, 1999; 274(30):21063–21070; *J. Biological Chemistry*, Aug. 27, 1999; 274(35):25188.

George, A.L. et al. "Assignment of the human heart tetrodotoxin–resistant voltage–gated $Na^+$ channel $\alpha$–subunit gene (SCN5A) to band 3p21", *Cytogenet. Cell Genet.*, 1995; 68:67–70.

Hoffman, E.P. et al. "Ion Channels—Molecular Divining Rods Hit Their Clinical Mark", *N. Engl. J. Med.*, May 29, 1997; 336(22):1599–1600.

Itoh, T. et al. "Genomic organization and mutational analysis of KVLQT1, a gene responsible for familial long QT syndrome", *Hum. Genet.*, 1998; 103:290–294.

Kambouris, N.G. et al. "A revised view of cardiac sodium channel "blockade" in the long–QT syndrome", *J. Clin. Invest.*, 2000; 105:1133–1140.

Kambouris, N.G. et al. "Phenotypic Characterization of a Novel Long–QT Syndrome Mutation (R1623Q) in the Cardiac Sodium Channel", *Circulation*, 1998; 97:640–644.

Keating, M. et al. "Consistent Linkage of the Long–QT Syndrome to the Harvey Ras–1 Locus on Chromosome 11", *Am. J. Hum. Genet.*, 1991; 49:1335–1339.

Keating, M.T. "Genetic Approaches to Cardiovascular Disease. Supravalvular Aortic Stenosis, Williams Syndrome, and Long–QT Syndrome", *Circulation*, 1995; 92:142–147.

Keating, M. et al. "Linkage of a Cardiac Arrhythmia, the Long QT Syndrome, and the Harvey ras–1 Gene", *Science*, May 3, 1991; 252:704–706.

Keating, M. et al. "Linkage Analysis and Long QT Syndrome. Using Genetics to Study Cardiovascular Disease", *Circulation*, 1992; 85:1973–1986.

Keating, M.T. "The Long QT Syndrome. A Review of Recent Molecular Genetic and Physiologic Discoveries", *Medicine*, 1996, 75(1):1–5.

Komsuoglu, B. et al. "The Jervell and Lange–Nielsen syndrome", *International Journal of Cardiology*, 1994; 47:189–192.

Krahn, A.D., et al. "A novel mutation in KVLQT1, L122P, found in a family with autosomal dominant long QT syndrome", *Am. Heart J.*, 2000; 140:146–149.

Larsen, L.A. et al. "A single strand conformation polymorphism/heteroduplex (SSCP/HD) method for detection of mutations in 15 exons of the KVLQT1 gene, associated with long QT syndrome", *Clinica Chimica Acta*, 1999; 280:113–125.

Larsen, L.A., et al. "High–Throughput Single–Strand Conformation Polymorphism Analysis by Automated Capillary Electrophoresis: Robust Multiplex Analysis and Pattern-Based Identification of Allelic Variants", *Human Mutation*, 1999; 13:318–327.

Lee, M.P., et al. "Human KVLQT1 gene shows tissue–specific imprinting and encompasses Beckwith–Wiedemann syndrome chromosomal rearrangements", *Nature Genetics*, Feb. 1997; 15:181–185.

Li, H. et al. "New Mutations in the KVLQT1 Potassium Channel That Cause Long–QT Syndrome", *Circulation*, 1998; 97:1264–1269.

Makita, N. et al. "Cardiac $Na^+$ Channel Dysfunction in Brugada Syndrome is Aggravated by $\beta_1$–Subunit", *Circulation*, 2000; 101:54–60.

Makita, N. et al. "A de novo missenge mutation of human cardiac Na⁺ channel exhibiting novel molecular mechanisms of long QT syndrome", *FEBS*, 1998; 423:5–9.

Mannens, M. et al. "KVLQT1, the rhythm of imprinting", *Nature Genetics*, Feb. 1997; 15:113–115.

Marx, J. "Rare Heart Disease Linked to Oncogene", *Research News*, May 3, 1997; p. 647.

Mohammad–Panah, R. et al. "Mutations in a Dominant–Negative Isoform Correlate with Phenotype in Inherited Cardiac Arrhythmias", *Am. J. Hum. Genet.*, 1999; 64:1015–1023.

Murray, A. et al. "Splicing Mutations in KCNQ1. A Mutation Hot Spot at Codon 344 That Produces in Frame Transcripts", *Circulation*, 1999; 100:1077–1074.

Neyroud, N. et al. "A novel mutation in the potassium channel gene KVLQT1 cuases the Jervell and Lange–Nielsen cardioauditory syndrome", *Nature Genetics*, Feb. 1997;15:186–189.

Neyroud, N. et al. "Heterozygous mutation in the pore of potassium channel gene KvLQT1 causes an apparently normal phenotype in long QT syndrome", *European Journal of Human Genetics*, 1998; 6:129–133.

Neyroud, N. et al. "Genomic Organization of the KCNQ1 K⁺ Channel Gene and Identification of C–Terminal Mutations in the Long–QT Syndrome", *Circ. Res.*, 1999; 84:290–297.

Pereon, Y. et al. "Differential expression of KvLQT1 isoforms across the human ventricular wall", *Am. J. Physiol. Heart Circ. Physiol.*, 2000; 278:H1908–H1915.

Priori, S. "Is long QT syndrome entering the era of molecular diagnosis?", *Heart*, 1997; 77:5–6.

Priori, S.G. et al. "A Recessive Variant of the Romano–Ward Long–QT Syndrome?", *Circulation*, 1998; 97:2420–2425.

Roden, D.M. et al. "Recent Advances in Understanding the Molecular Mechanisms of the Long QT Syndrome", *J. Cardiovasc. Electrophysiol.*, Nov. 1995; 6:1023–1031.

Romey, G. et al. "Molecular Mechanism and Functional Significance of the MinK Control of the KvLQT1 Channel Activity", *J. Biological Chemistry*, Jul. 4, 1997; 272(27):16713–16716.

Rook, M.B. et al. "Human SCN5A gene mutations alter cardiac sodium channel kinetics and are associated with the Brugada syndrome", *Cardiovascular Research*, 1999; 44:507–517.

Rosen, M.R. "Long QT Syndrome Patients with Gene Mutations", *Circulation*, Dec. 15, 1995; 92(12):3373–3375.

Russell, M.W. "KVLQT1 mutations in three families with familial or sporadic long QT syndrome", *Human Molecular Genetics*, 1996; 5(9):1319–1324.

Sanguinetti, M.C. et al. "Coassembly of K$_v$LQT1 and minK (IsK) proteins to form cardiac I$_{ks}$ potassium channel", *Nature*, Nov. 7, 1996; 384:80–83.

Sanguinetti, M.C. et al. "Potassium Channelopathies", *Neuropharmacology*, 1997; 36(6):755–762.

Schmitt, N. et al. "A recessive C–terminal Jervell and Lange–Nielsen mutation of the KCNQ1 channel impairs subunit assembly", *The EMBO Journal*, 2000; 19(3):332–340.

Schott, J.–J. et al. "Cardiac conduction defects associate with mutations in SCN5A", *Nature Genetics*, Sep. 1999; 23:20–21.

Schwartz, P.J. et al. "Long QT Syndrome Patients with Mutations of the SCN5A and HERG Genes Have Differential Responses to Na⁺ Channel Blockade and to Increases in Heart Rate", *Circulation*, 1995; 92:3381–3386.

Schwartz, P.J. et al. "A Molecular Link Between the Sudden Infant Death Syndrome and the Long–QT Syndrome", *N. Engl. J. Med.*, Jul. 27, 2000; 343(4):262–267.

Shalaby, F.Y. et al. "Dominant–Negative KvLQT1 Mutations Underlie the LQT1 Form of Long QT Syndrome", *Circulation*, 1997; 96:1733–1736.

Shimizu, W. et al. "Improvement of Repolarization Abnormalities by a K⁺ Channel Opener in the LQT1 Form of Congenital Lont–QT Syndrome", *Circulation*, 1998; 97:1581–1588.

Splawski, I. et al. "Molecular Basis of the Long–QT Syndrome Associated with Deafness", *N. Engl. J. Med.*, May 29, 1997; 336(22):1562–1567.

Splawski, I. et al. "Genomic Structure of Three Long QT Syndrome Genes: KVLQT1, HERG, and KCNE1", *Genomics*, 1998; 51:86–97.

Tanaka, T. et al. "Four Novel KVLQT1 and Four Novel HERG Mutations in Familial Long–QT Syndrome", *Circulation*, 1997; 95:565–567.

Towbin, J.A. et al. "Evidence of Genetic Heterogeneity in Romano–Ward Long QT Syndrome", *Circulation*, 1994; 90:2635–2644.

Tyson, J. et al. "IsK and KvLQT1: mutation in either of the two subunits of the slow component of the delayed rectifier potassium channel can cause Jervell and Lange–Nielsen syndrome", *Human Molecular Genetics*, 1997; 6(12):2179–2185.

Tyson, J. et al. "Splice Mutations In KVLQT1?", *Circulation*, 1999; 99(18):2476–2477.

Van Den Berg, M.H. et al. "The long QT syndrome: a novel missense mutation in the S6 region of the KVLQT1 gene", *Hum. Genet.*, 1997; 100:356–361.

Vincent, G.M. "The Molecular Genetics of the Long QT Syndrome: Genes Causing Fainting and Sudden Death", *Annu. Rev. Med.*, 1998; 49:263–274.

Vincent, G.M. "Genetics and Molecular Biology of the Inherited Long QT Syndrome", *Annals of Medicine*, 1994; 26:419–425.

Wang, D.W. et al. "Characterization of human cardiac Na⁺ channel mutations in the congenital long QT syndrome", *Proc. Natl. Acad. Sci. USA*, Nov. 1996; 93:13200–13205.

Wang, Q. et al. "Cardiac sodium channel mutations in patients with long QT syndrome, an inherited cardiac arrhythmia", *Human Molecular Genetics*, 1995; 4(9):1603–1607.

Wang, Q. et al. "Molecular genetics of long QT syndrome from genes to patients", *Current Opinion in Cardiology*, 1997; 12:310–320.

Wang, Q. et al. "Positional cloning of a novel potassium channel gene: KVLQT1 mutations cause cardiac arrhythmias", *Nature Genetics*, Jan. 1996; 12:17–23.

Wang, Q. et al. "SCN5A Mutations Associated with an Inherited Cardiac Arrhythmia, Long QT Syndrome", *Cell*, Mar. 10, 1995; 90:805–811.

Wattanasirichaigoon, D. et al. "Sodium Channel Abnormalities are Infrequent in Patients with Long QT Syndrome: Identification of Two Novel SCN5A Mutations", *Am. J. Med. Genet.*, 1999; 86:470–476.

Wei, J. et al. "Congenital Long–QT Syndrome Caused by a Novel Mutation in a Conserved Acidic Domain of the Cardiac Na$^+$ Channel", *Circulation*, 1999; 99:3165–3171.

Wollnik, B. et al. "Pathophysiological mechanisms of dominant and recessive KVLQT1 K$^+$ channel mutations found in inherited cardiac arrhythmias", *Human Molecular Genetics*, 1997; 6(11):1943–1949.

Yang, W.–P. et al. "KvLQT1, a voltage–gated potassium channel responsible for human cardiac arrhythmias", *Proc. Natl. Acad. Sci. USA*, Apr. 1997; 94:4017–4021.

Chouabe, C. et al. "Properties of KvLQT1 K$^+$ channel mutations in Romano–Ward and Jervell and Lange–Nielsen inherited cardiac arrhythmias", Accession No. AF000571; 3 pp.

http://www.ncbi.nlm.nih.gov; GenBank Accession No. U86146; Yang, W.P. et al. "KvLQT1, a voltage–gated potassium channel responsible for human cardiac arrhythmias", 2pp.

http://www.ncbi.nlm.nih.gov; OMIM Entry 600163; 11 pp.

http://www.ncbi.nlm.nih.gov; OMIM Entry 192500; 27 pp.

* cited by examiner

US 6,342,357 B1

ALTERATIONS IN THE LONG QT SYNDROME GENES KVLQT1 AND SCN5A AND METHODS FOR DETECTING SAME

CROSS REFERENCE TO RELATED APPLICATIONS

The present invention is related to provisional application Ser. No. 60/190,057 filed Mar. 17, 2000, and is also related to provisional application Ser. No. 60/147,488 filed Aug. 9, 1999, both of which are incorporated herein by reference.

This application was made with Government support from NHLBI under Grant Nos. RO1-HL46401, RO1-HL33843, RO1-HL51618, P50-HL52338 and MO1-RR000064. The federal government may have certain rights in this invention.

BACKGROUND OF THE INVENTION

Long QT Syndrome (LQTS) is a cardiovascular disorder characterized by prolongation of the QT interval on electrocardiogram and presence of syncope, seizures and sudden death, usually in young, otherwise healthy individuals (Jervell and Lange-Nielsen, 1957; Romano et al., 1963; Ward, 1964). The clinical features of LQTS result from episodic ventricular tachyarrhythmias, such as torsade de pointes and ventricular fibrillation (Schwartz et al., 1975; Moss et al., 1991). Two inherited forms of LQTS exist. The more common form, Romano-Ward syndrome (RW), is not associated with other phenotypic abnormalities and is inherited as an autosomal dominant trait with variable penetrance (Roman et al., 1963; Ward, 1964). Jervell and Lange-Nielsen syndrome (JLN) is characterized by the presence of deafness, a phenotypic abnormality inherited as an autosomal recessive trait (Jervell and Lange-Nielsen, 1957). LQTS can also be acquired, usually as a result of pharmacologic therapy.

In previous studies, we mapped LQTS loci to chromosomes 11p15.5 (LQT1) (Keating et al., 1991), 7 q35–36 (LQT2) (Jiang et al., 1994) and LQT3 to 3p21–24 (Jiang et al., 1994). A fourth locus (LQT4) was mapped to 4q25–27 (Schott et al., 1995). Five genes have been implicated in Romano-Ward syndrome, the autosomal dominant form of LQTS. These genes are KVLQT1 (LQT1) (Wang Q. et al., 1996a), HERG (LQT2) (Curran et al., 1995), SCN5A (LQT3) (Wang et al., 1995a), and two genes located at 21q22—KCNE1 (LQT5) (Splawski et al., 1997a) and KCNE2 (LQT6) (Abbott et al., 1999). Mutations in KVLQT1 and KCNE1 also cause the Jervell and Lange-Nielsen syndrome, a form of LQTS associated with deafness, a phenotypic abnormality inherited in an autosomal recessive fashion.

KVLQT1, HERG, KCNE1 and KCNE2 encode potassium channel subunits. Four KVLQT1 α-subunits assemble with minK (β-subunits encoded by KCNE1, stoichiometry is unknown) to form $I_{Ks}$ channels underlying the slowly activating delayed rectifier potassium current in the heart (Sanguinetti et al., 1996a; Barhanin et al., 1996). Four HERG α-subunits assemble with MiRP1 (encoded by KCNE2, stoichiometry unknown) to form $I_{Kr}$ channels, which underlie the rapidly activating, delayed rectifier potassium current (Abbott et al., 1999). Mutant subunits lead to reduction of $I_{Ks}$ or $I_{Kr}$ by a loss-of-function mechanism, often with a dominant-negative effect (Chouabe et al., 1997; Shalaby et al., 1997; Wollnik et al., 1997; Sanguinetti et al. 1996b). SCN5A encodes the cardiac sodium channel that is responsible for $I_{Na}$, the sodium current in the heart (Gellens et al., 1992). LQTS-associated mutations in SCAN5A cause a gain-of-function (Bennett et al., 1995; Dumaine et al., 1996). In the heart, reduced $I_{Ks}$ or $I_{Kr}$ or increased $I_{Na}$ leads to prolongation of the cardiac action potential, lengthening of the QT interval and increased risk of arrhythlumia. KVLQT1 and KCNE1 are also expressed in the inner ear (Neyroud et al., 1997; Vetter et al., 1996). Others and we demonstrated that complete loss of $I_{Ks}$ causes the severe cardiac phenotype and deafness in JLN (Neyroud et al., 1997; Splawski et al., 1997b; Tyson et al., 1997; Schulze-Bahr et al., 1997).

Presymptomatic diagnosis of LQTS is currently based on prolongation of the QT interval on electrocardiogram. Genetic studies, however, have shown that diagnosis based solely on electrocardiogram is neither sensitive nor specific (Vincent et al., 1992; Priori et al., 1999). Genetic screening using mutational analysis can improve presymptomatic diagnosis. However, a comprehensive study identifying and cataloging all LQTS-associated mutations in all five genes has not been achieved. To determine the relative frequency of mutations in each gene, facilitate presymptomatic diagnosis and enable genotype-phenotype studies, we screened a pool of 262 unrelated individuals with LQTS for mutations in the five defined genes. The results of these studies are presented in the Examples below.

The present invention relates to alterations in the KVLQT1, HERG, SCN5A, KCNE1 and KCNNE2 genes and methods for detecting such alterations.

The publications and other materials used herein to illuminate the background of the invention or provide additional details respecting the practice, are incorporated by reference, and for convenience are respectively grouped in the appended List of References.

The present invention is directed to alterations in genes and gene products associated with long QT syndrome and to a process for the diagnosis and prevention of LQTS. LQTS is diagnosed in accordance with the present invention by analyzing the DNA sequence of the KVLQT1, HERG, SCN5A, KCNE1 or KCNE2 gene of an individual to be tested and comparing the respective DNA sequence to the known DNA sequence of the normal gene. Alternatively, these genes of an individual to be tested can be screened for mutations which cause LQTS. Prediction of LQTS will enable practitioners to prevent this disorder using existing medical therapy.

SUMMARY OF THE INVENTION

The present invention relates to alterations in the KVLQT1, HERG, SCN5A, KCNE1 and KCNE2 genes and methods for detecting such alterations. The alterations in the KVLQT1, HERG, SCN5A, KCNE1 and KCNE2 genes include mutations and polymorphisms. Included among the mutations are frameshift, nonsense, splice, regulatory and missense mutations. Any method which is capable of detecting the alterations described herein can be used. Such methods include, but are not limited to, DNA sequencing, allele-specific probing, mismatch detection, single stranded conformation polymorphism detection and allele-specific PCR amplification.

DETAILED DESCRIPTION OF THE INVENTION

Figure 1:
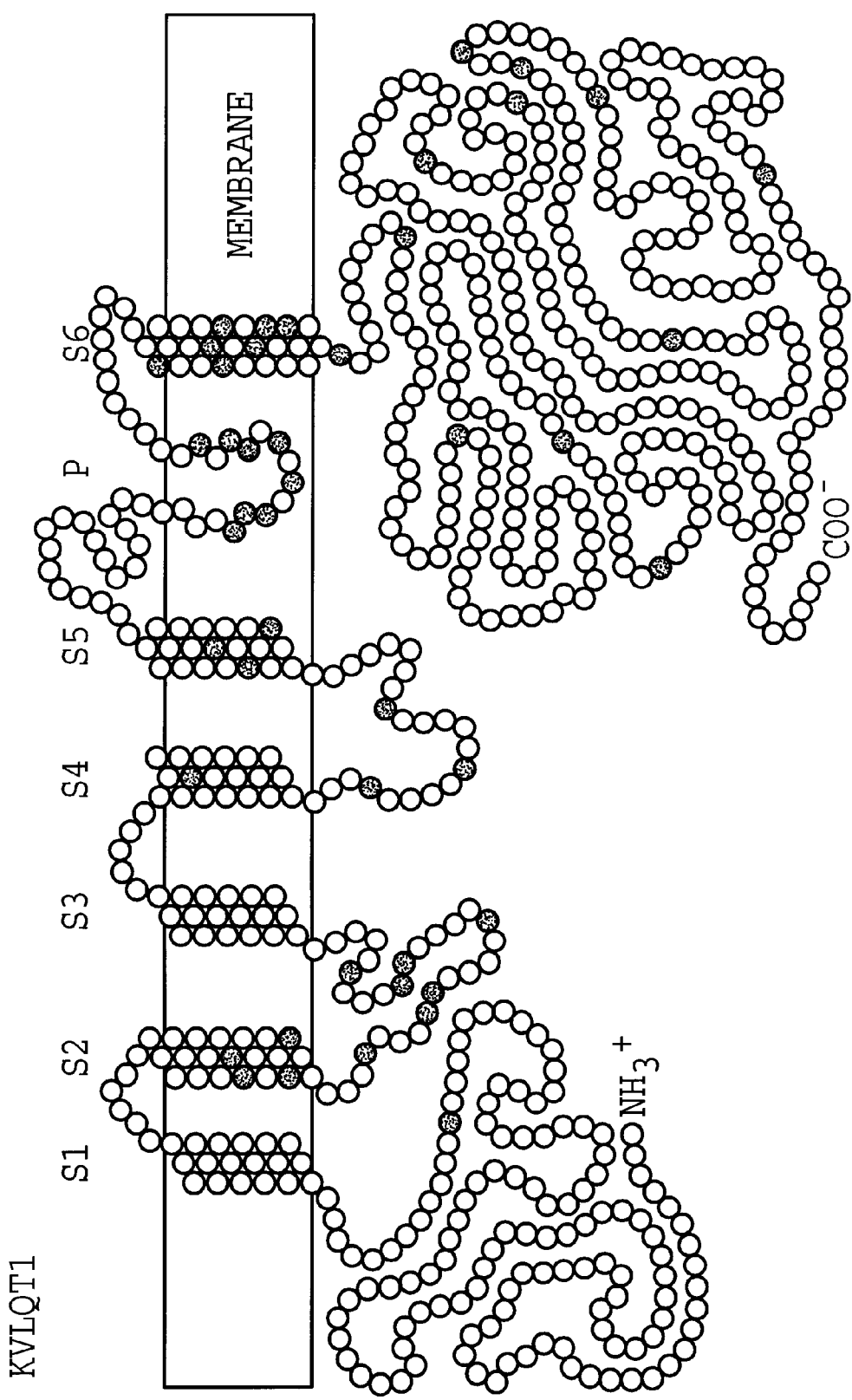
FIG. 1 is a schematic representation of the predicted topology of KVLQT1 and the locations of LQTS-associated mutations. KVLQT1 consists of six putative transmembrane segments (S1 to S6) and a pore (Pore) region. Each circle represents an amino acid. The approximate location of LQTS-associated mutations identified in our laboratory are shown with filled circles.

The present invention relates to alterations in the KVLQT1, HERG, SCN5A, KCNE1 and KCNE2 genes and methods for detecting such alterations. The alterations in the KVLQT1, HERG, SCN5A, KCNE1 and KCNE2 genes include mutations and polymorphisms. Included among the mutations are frameshift, nonsense, splice, regulatory and missense mutations. Any method which is capable of detecting the mutations and polymorphisms described herein can be used. Such methods include, but are not limited to, DNA sequencing, allele-specific probing, mismatch detection, single stranded conformation polymorphism detection and allele-specific PCR amplification.

KVLQT1, HERG, SCN5A, KCNE1 and KCNE2 mutations cause increased risk for LQTS. Many different mutations occur in KVLQT1, HERG, SCN5A, KCNE1 and KCNE2. In order to detect the presence of alterations in the KVLQT1, HERG, SCN5A, KCNE1 and KCNE2 genes, a biological sample such as blood is prepared and analyzed for the presence or absence of a given alteration of KVLQT1, HERG, SCN5A, KCNE1 or KCNE2. In order to detect the increased risk for LQTS or for the lack of such increased risk, a biological sample is prepared and analyzed for the presence or absence of a mutant allele of KVLQT1, HERG, SCN5A, KCNE1 or KCNE2. Results of these tests and interpretive information are returned to the health care provider for communication to the tested individual. Such diagnoses may be performed by diagnostic laboratories or, alternatively, diagnostic kits are manufactured and sold to health care providers or to private individuals for self-diagnosis.

The presence of hereditary LQTS may be ascertained by testing any tissue of a human for mutations of the KVLQT1, HERG, SCN5A, KCNE1 or KCNE2 gene. For example, a person who has inherited a germline HERG mutation would be prone to develop LQTS. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the KVLQT1, HFRG, SCN5A, KCNE1 or KCNE2 gene. Alteration of a wild-type KVLQT1, HERG, SCN5A, KCNE1 or KCNE2 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQTS cases. Southern blots displaying hybridizing fragments (differing in length from control DNA when probed with sequences near or including the HERG locus) indicate a possible mutation. If restriction enzymes which produce very large restriction fragments are used, then pulsed field gel electrophoresis (PFGE) is employed.

Detection of point mutations may be accomplished by molecular cloning of the KVLQT1, HERG, SCN5A, KCNE1 or KCNE2 alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Filklelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular KVLQT1, HERG, SCN5A, KCNE1 or KCNE2 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DCGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KVLQT1, HERG, SCN5A, KCNE1 or KCNE2 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the KVLQT1, HERG, SCN5A, KCNE1 or KCNE2 gene can also be detected using Southern hybridization, especially if the changes are gross rearrangements, such as deletions and insertions.

DNA sequences of the KVLQT1, HERG, SCN5A, KCNE1 or KCNE2 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified KVLQT1, HERG, SCN5A, KCNE1 or KCNE2 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic KVLQT1, HERG, SCN5A, KCNE1 or KCNE2 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KVLQT1, HERG, SCN5A, KCNE1 or KCNE2 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KVLQT1, HERG, SCN5A, KCNE1 or KCNE2 mRNA expression can be detected by any techniques known in the art. These include Northern blot analysis, PCR amplification and RNase protection. Diminished mRNA expression indicates an alteration of the wild-type gene. Alteration of wild-type (genes can also be detected by screening for alteration of wild-type KVLQT1, HERG, SCN5A, KCNE1 or KCNE2 protein. For example, monoclonal antibodies immunoreactive with HERG can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered KVLQT1, HERG, SCN5A, KCNE1 or KCNE2 protein can be used to detect alteration of wild-type KVLQT1, HERG, SCN5A, KCNE1 or KCNE2 genes. Functional assays, such as protein binding determinations, can be used. In addition, assays can be used which detect KVLQT1, HERG, SCN5A, KCNE1 or KCNE2 biochemical function. Finding a mutant KVLQT1, HERG, SCN5A, KCNE1 or KCNE2 gene product indicates alteration of a wild-type KVLQT1, HERG, SCN5A, KCNE1 or KCNE2 gene.

Mutant KVLQT1, HERG, SCN5A, KCNE1 or KCNE2 genes or gene products can also be detected in other human body samples, such as serum, stool, urine and sputum. The same techniques discussed above for detection of mutant genes or gene products in tissues can be applied to other body samples. By screening such body samples, a simple early diagnosis can be achieved for hereditary LQTS.

Initially, the screening method involves amplification of the relevant KVLQT, HERG, SCN5A, KCNE1 or KCNE2 sequence. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity. Further details of these methods are briefly presented below and further descriptions can be found in PCT published application WO 96/05306, incorporated herein by reference.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences, the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of the genes. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are well known.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently lined to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity For example, the preparation of oligodeoxynucleotide-alkaline phosphatase conjugates and their use as hybridization probes are well known.

Two-step label amplification methodologies are known in the art. These assays work on the principle that a small ligand (such as digoxigenin, biotin, or the like) is attached to a nucleic acid probe capable of specifically binding the target gene. Allele specific probes are also contemplated within the scope of this example.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type of interactions. Methods for labeling nucleic acid probes and their use in biotin-avidin based assays are well known.

It is also contemplated within the scope of this invention that the nucleic acid probe assays of this invention will employ a cocktail of nucleic acid probes capable of detecting the gene or genes. Thus in one example to detect the presence of KVLQT1 in a cell sample, more than one probe complementary to KVLQT1 is employed and in particular the number of different probes is alternatively 2, 3, or 5 different nucleic acid probe sequences. In another example, to detect the presence of mutations in the KVLQT1 gene sequence in a patient, more than one probe complementary to KVLQT1 is employed where the cocktail includes probes capable of binding to the allele-specific mutations identified in populations of patients with alterations in KVLQT1. In this embodiment, any number of probes can be used.

Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al. (1989) or Ausubel et al. (1992).

An appropriate promoter and other necessary vector sequences will be selected so as to be functional in the host, and may include, when appropriate, those naturally associated with the KVLQT1 or other gene. Examples of workable combinations of cell lines and expression vectors are described in Sambrook et al. (1989) or Ausubel et al. (1992); see also, e.g., Metzger et al. (1988). Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al. (1988)), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al. (1989) and Ausubel et al. (1992). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KVLQT1 nucleic acid or portions thereof in vectors or other expression vehicles in compatible prokaryotic or eukaryotic host cells. The most commonly used prokaryotic hosts are strains of *Escherichia coli,* although other prokaryotes, such as *Bacilluis subtilis* or Pseudonmonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of KVLQT1 or other polypeptides.

The probes and primers based on the KVLQT1 or other gene sequences disclosed herein are used to identify homologous KVLQT1 or other gene sequences and proteins in other species. These gene sequences and proteins are used in the diagnostic/prognostic, therapeutic and drug screening methods described herein for the species from which they have been isolated.

The studies described in the Examples below resulted in the determination of many novel mutations. Previous studies had defined 126 distinct disease causing mutations in the LIQTS genes KVLQT1, HERG, SCN5A, KCNE1 and KCNE2 (Wang Q. et al., 1996a; Curran et al., 1995; Wang et al., 1995a; Splawski et al., 1997a; Abbott et al., 1999; Chouabe et al., 1997; Wollnik et al., 1997; Neyroud et al., 1997; Splawski et al., 1997b; Tyson et al., 1997; Schulze-Bahr et al., 1997; Priori et al., 1999; Splawski et al., 1998; Wang et al., 1995b; Russell et al., 1996; Neyroud et al., 1998; Neyroud et al., 1999; Donger et al., 1997; Tanaka et al., 1997; Jongbloed et al., 1999; Priori et al., 1998; Itoh et al., 1998a; Itoh et al., 1998b; Mohammad-Panah et al., 1999; Saarinen et al., 1998; Ackerman et al., 1998; Berthet et al., 1999; Kanters, 1998; van den Berg et al., 1997; Dausse et al., 1996; Benson et al., 1996; Akimoto et al., 1998; Satler et al., 1996; Satler et al., 1998; Makita et al., 1998, An et al., 1998; Schulze-Bahr et al., 1995; Duggal et al., 1998; Chen Q. et al., 1999; Li et al., 1998; Wei et al., 1999; Larsen et al., 1999a; Bianchi et al., 1999; Ackerman et al., 1999a; Ackerman et al., 1999b; Murray et al., 1999; Larsen et al., 1999b; Yoshida et al., 1999; Wattanasirichaigoon et al., 1999; Bezzina et al., 1999; Hoorntje et al., 1999). The sequence of each wild-type gene has been published. The KVLQT1 can be found in Splawski et al. (1998) and the coding region of the cDNA is shown herein as SEQ ID NO:1 and the encoded KVLQT1 is shown as SEQ ID NO:2. SCN5A was reported by Gellens et al. (1992) and its sequence is provided by GenBank Accession No. NM_000335. The coding sequence of SCN5A is shown herein as SEQ ID NO:3 and the encoded SCN5A is shown as SEQ ID NO:4. Most of the mutations were found in KVLQT1 (Yoshida et al., 1999) and HERG (Itoh et al., 1998b), and fewer in SCN5A (Wang Q. et al., 1996a), KCNE1 (Jiang et al., 1994) and KCNE2 (Ward, 1964). These mutations were identified in regions with known intron/exon structure, primarily the transmembrane and pore domains. In this study, we screened 262 individuals with LQTS for mutations in all known arrhythmia genes. We identified 134 mutations, 80 of which were novel. Together with 43 mutations reported in our previous studies we have now identified 177 mutations in these 262 LQTS individuals (68%). The failure to identify mutations in 32% of the individuals may result from phenotypic errors, incomplete sensitivity of SSCP or presence of mutations in regulatory sequences. However, it is also clear that additional LQTS genes await discovery (Jiang et al., 1994; Schott et al., 1995).

Missense mutations were most common (72%), followed by frameshift mutations (10%), in-frame deletions, nonsense and splice site mutations (5–7% each). Most mutations resided in intracellular (52%) and transmembrane (30%) domains; 12% were found in pore and 6% in extracellular segments. One hundred one of the 129 distinct LQTS mutations (78%) were identified in single families or individuals. Most of the 177 mutations were found in KVLQT1 (75 or 42%) and HERG (80 or 45%). These two genes accounted for 87% of the identified mutations, while mutations in SCN5A (14 or 8%), KCNE1 (5 or 3%) and KCNE2 (3 or 2%) accounted for the other 13%.

Multiple mutations were found in regions encoding S5, S5/P, P and S6 of KVLQT1 and HERG. The P region of potassium channels forms the outer pore and contains the selectivity filter (Doyle et al., 1998). Transmembrane segment 6, corresponding to the inner helix of KcsA, forms the inner 2/3 of the pore. This structure is supported by the S5 transmembrane segment, corresponding to the outer helix of KcsA, and is conserved from prokaryotes to eukaryotes ((MacKinnon et al., 1998). Mutations in these regions will likely disrupt potassium transport. Many mutations were identified in the C-termini of KVLQT1 and HERG. Changes in the C-terminus of HERG could lead to anomalies in tetramerization as it has been proposed that the C-terminus of eag, which is related to HERG, is involved in this process (Ludwig et al, 1994).

Multiple mutations were also identified in regions that were different for KVLQT1 and HERG. In KVLQT1, multiple mutations were found in the sequences coding for the S2/S3 and S4/S5 linkers. Coexpression of S2/S3 mutants with wild-type KVLQT1 in Xenopus oocytes led to simple loss of function or dominant-negative effect without significantly changing the biophysical properties of $I_{Ks}$ channels (Chouabe et al., 1997; Shalaby et al., 1997; Wang et al., 1999). On the other hand, S4/S5 mutations altered the gating properties of the channels and modified KVLQT1 interactions with minK subunits (Wang et al., 1999; Franqueza et al., 1999). In HERG, more than 20 mutations were identified in the N-terminus. HERG channels lacking this region deactivate faster and mutations in the region had a similar effect (Chen J. et al., 1999).

Mutations in KCNE1 and KCNE2, encoding minK and MiRP1, the respective $I_{Ks}$ and $I_{Kr}$ β-subunits, altered the biophysical properties of the channels (Splawski et al., 1997a; Abbott et al., 1999; Sesti and Goldstein, 1998). A MiRP1 mutant, involved in clarithromyocin-induced arrhythmia, increased channel blockade by the antibiotic (Abbott et al., 1999). Mutations in SCN5A, the sodium channel α-subunit responsible for cardiac $I_{Na}$, destabilized the inactivation gate causing delayed channel inactivation and dispersed reopenings (Bennett et al., 1995; Dumaine et al., 1996; Wei et al., 1999; Wang DW et al., 1996). One SCN5A mutant affected the interactions with the sodium channel β-subunit (An et al., 1998).

It is interesting to note that probands with KCNE1 and KCNE2 mutations were older and had shorter QTc than probands with the other genotypes. The significance of these differences is unknown, however, as the number of probands with KCNE1 and KCNE2 genotypes was small.

This catalogue of mutations will facilitate genotype-phenotype analyses. It also has clinical implications for presymptomatic diagnosis and, in some cases, for therapy. Patients with mutations in KVLQT1, HERG, KCNE1 and KCNE2, for example, may benefit from potassium therapy (Compton et al., 1996). Sodium channel blockers, on the other hand, might be helpful in patients with SCN5A mutations (Schwartz et al. (1995). The identification of mutations is of importance for ion channel studies as well. The expression of mutant channels in heterologous systems can reveal how structural changes influence the behavior of the channel or how mutations affect processing (Zhou et al., 1998; Furutani et al., 1999). These studies improve our understanding of channel function and provide insights into mechanisms of disease. Finally, mutation identification will contribute to the development of genetic screening for arrhythmia susceptibility.

The present invention is described by reference to the following Examples, which are offered by way of illustration and are not intended to limit the invention in any manner. Standard techniques well known in the art or the techniques specifically described in the Examples were utilized.

EXAMPLE 1

Ascertainment and Phenotyping

Individuals were ascertained in clinics from North America and Europe. Individuals were evaluated for LQTS based on QTc (the QT interval corrected for heart rate) and for the presence of symptoms. In this study, we focused on the probands. Individuals show prolongation of the QT interval (QTc≧460 ms) and/or documented torsade de pointes, ventricular fibrillation, cardiac arrest or aborted sudden death. Informed consent was obtained in accordance with local institutional review board guidelines. Phenotypic data were interpreted without knowledge of genotype. Sequence changes altering coding regions or predicted to affect splicing that were not detected in at least 400 control chromosomes were defined as mutations. No changes except known polymorphisms were detected ina ny of the genes in the control population. This does not exclude the possibility that some mutations are rare variants not associated with disease.

EXAMPLE 2

Mutational Analyses

To determine the spectrum of IQTS mutations, we used SSCP (Single Stand Conformation Polymorphism) and DNA sequence analyses to screen 262 unrelated individuals with LQTS. Seventeen primer pairs were used to screen KVLQT1 (Splawski et al., 1998), twenty-one primer pairs were used for HERG (Splawski et al., 1998) and three primer pairs were used for KCNE1 (Splawski et al., 1997a) and KCNE2 (Abbott et al., 1999). Thirty-three primer pairs (Wang Q. et al., 1996b) were used in SSCP analysis to screen all SCN5A exons in 50 individuals with suspected abnormalities in $I_{Na}$. Exons 23–28, in which mutations were previously identified, were screened in all 262 individuals.

Gender, age, QTc and presence of symptoms are summarized in Table 1. The average age at ascertainment was 29 with a corrected QT interval of 492 ms. Seventy-five percent had a history of symptoms and females predominated with an ~2:1 ratio. Although the numbers were small, corrected QT intervals for individuals harboring KCNE1 and KCNE2 mutations were shorter at 457 ms.

TABLE 1

Age, QTc, Gender and Presence of Symptoms

| Genotype | Age*, y (mean ± SD) | Gender (F/M) | QTc, ms (mean ± SD) | Symptoms[†] |
|---|---|---|---|---|
| KVLQT1 | 32 ± 19 | 52/23 | 493 ± 45 | 78% |
| HERG | 31 ± 19 | 51/29 | 498 ± 48 | 71% |
| SCN5A | 32 ± 24 | 8/6 | 511 ± 42 | 55% |
| KCNE1 | 43 ± 16 | 3/2 | 457 ± 25 | 40% |
| KCNE2 | 54 ± 20 | 3/0 | 457 ± 05 | 67% |
| unknown | 25 ± 16 | 56/29 | 484 ± 46 | 81% |
| all | 29 ± 19 | 173/89 | 492 ± 47 | 75% |

Figure 2:
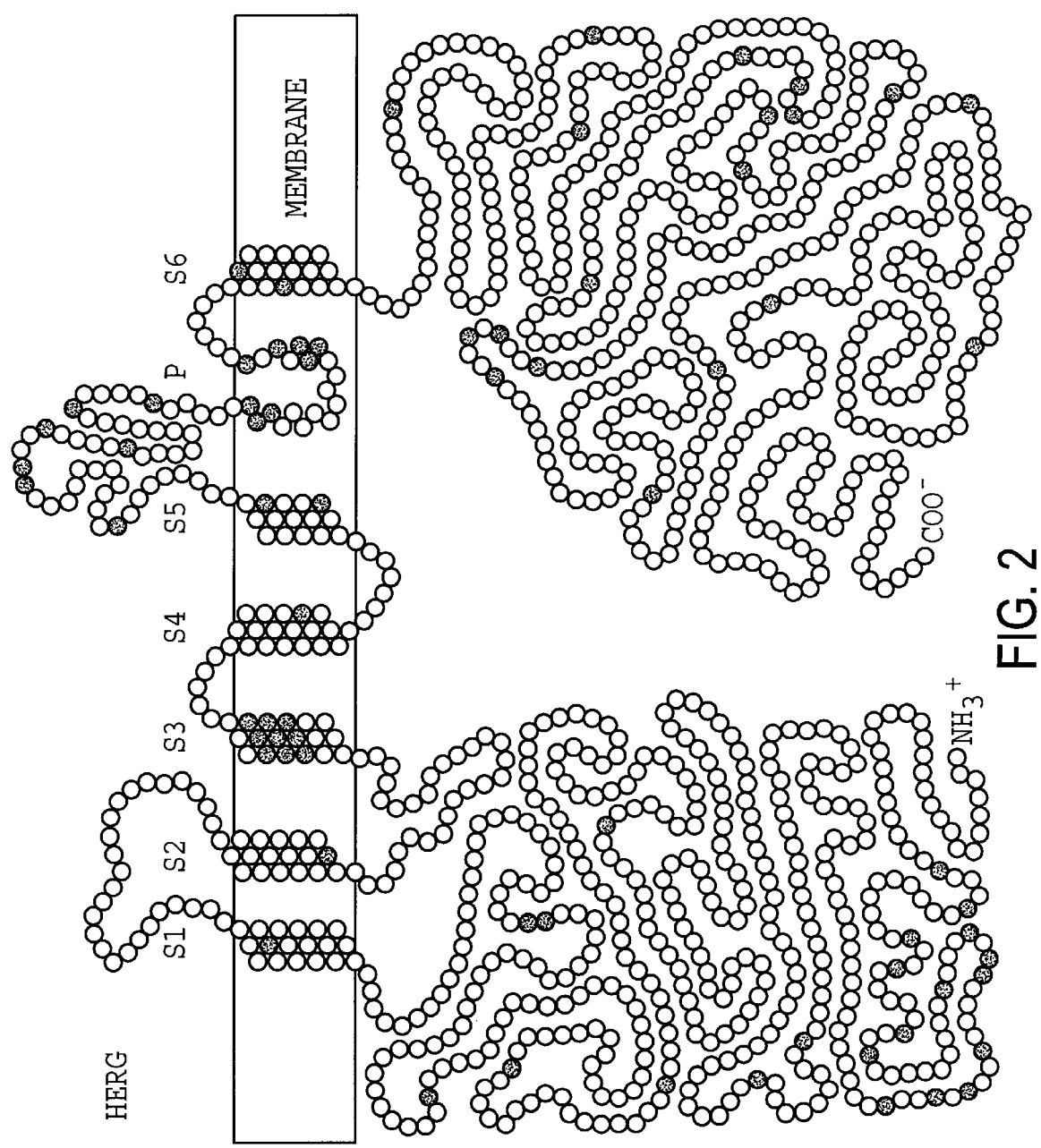
FIG. 2 is a schematic representation of HERG mutations. HERG consists of six putative transmembrane segments (S1 to S6) and a pore (Pore) region. Location of LQTS-associated mutations are shown with filled circles.
Figure 3:
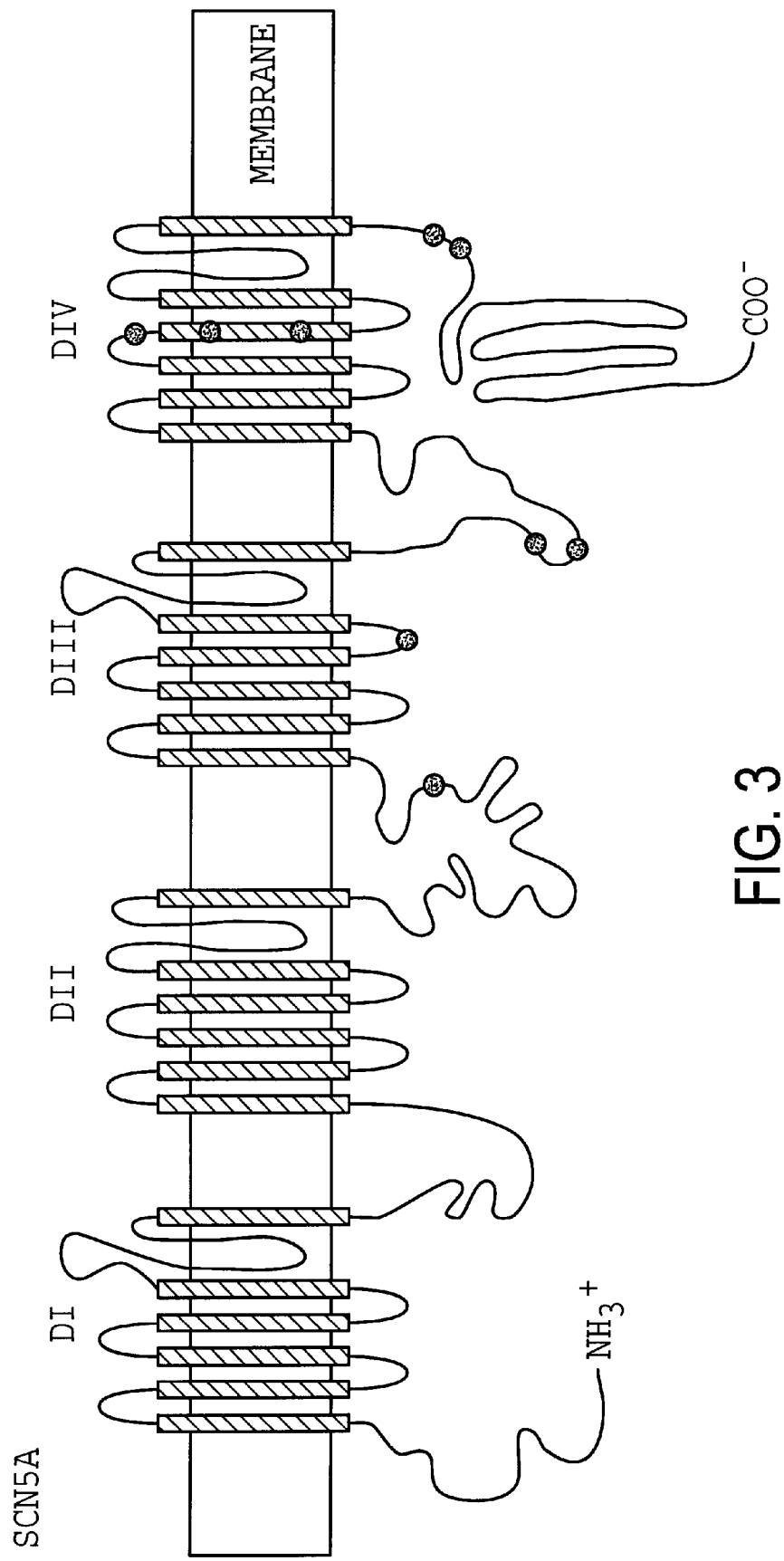
FIG. 3 is a schematic representation of SCN5A and locations of LQTS-associated mutations. SCN5A consists of four domain (DI to DIV), each of which has six putative transmembrane segments (S1 to S6) and a pore (Pore) region. Location of LQTS-associated mutations identified in our laboratory are shown with filled circles.
Figure 4:
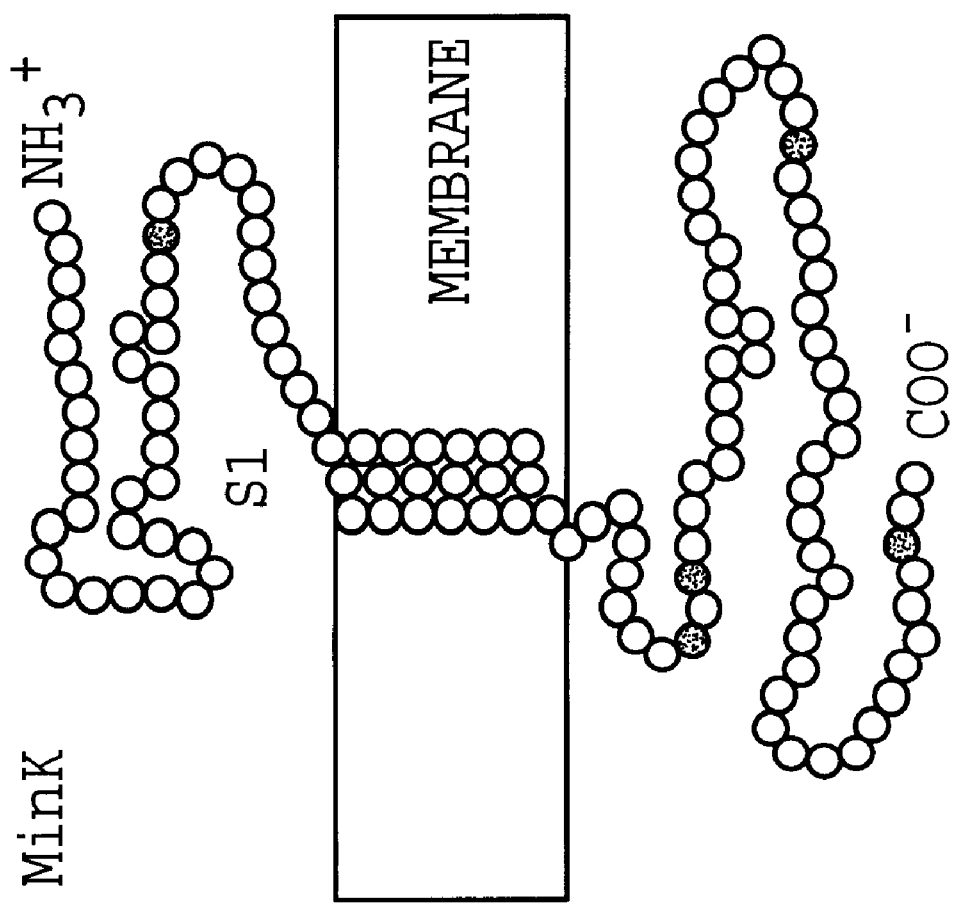
FIG. 4 is a schematic representation of minK and locations of LQT-associated mutations. MinK consists of one putative transmembrane domain (S1). The approximate location of LQTS-associated mutations identified in our laboratory are shown with filled circles.
Figure 5:
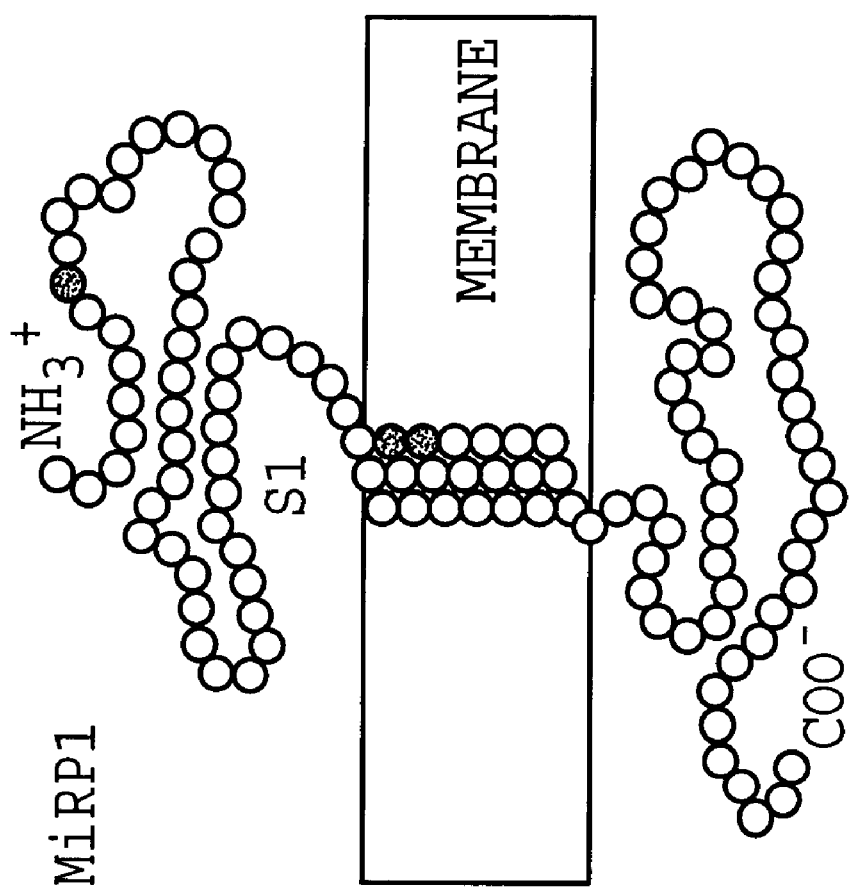
FIG. 5 is a schematic representation of the predicted topology of MiRP1 and locations of arrhythmia-associated mutations. MiRP1 consists of one putative transmembrane domain (S1). The approximate location of arrhythmia-associated mutations identified in our laboratory are shown with filled circles.

*age at ascertainment
[†]symptoms include syncope, cardiac arrest or sudden death The SSCP analyses revealed many mutations. KVLQT1 mutations associated with LQTS were identified in 52 individuals (FIG. 1 and Table 2). Twenty of the mutations were novel. HERG mutations were identified in 68 LQTS individuals (FIG. 2 and Table 3). Fifty-two of these mutations were novel. SCN5A mutations were identified in eight cases (FIG. 3 and Table 4). Five of the mutations were novel. Three novel KCNE1 mutations were identified (FIG. 4 and Table 5) and three mutations were identified in KCNE2 (FIG. 5 and Table 6) (Abbott et al., 1999). None of the KVLQT1, HERG, SCN5A, KCNE1 and KCNE2 mutations was observed in 400 control chromosomes.

TABLE 2

Summary of All KVLQT1 Mutations*

| Nucleotide Change[†] | Coding Effect | Position | Exon | Number of families[‡] | Study |
|---|---|---|---|---|---|
| del211–219 | del71–73 | N-terminus | 1 | 1 | Ackerman et al., 1999a |
| A332G[†] | Y111C | N-terminus | 1 | 1 | This |
| del451–452 | A150fs/132 | S2 | 2 | 1 JLN | Chen Q. et al., 1999 |
| T470G | F157C | S2 | 1 | 1 | Larsen et al., 1999a |
| G477 + 1A | M159sp | S2 | 2 | 1 JLN, 1 UK | This; Donger et al., 1997 |
| G477 + 5A | M159sp | S2 | 1 | 1 | Ackerman et al., 1999b |
| G478A[†] | E160K | S2 | 3 | 1 | This |
| del500–502 | F167W/del G168 | S2 | 3 | 1 | Wang Q. et al., 1996a |
| G502A | G168R | S2 | 3 | 7 | This; Splawski et al., 1998; Donger et al., 1997 |
| C520T | R174C | S2/S3 | 3 | 1 | Donger et al., 1997 |
| G521A[†] | R174H | S2/S3 | 3 | 1 | This |
| G532A | A178T | S2/S3 | 3 | 1 | Tanaka et al., 1997 |
| G532C | A178P | S2/S3 | 3 | 1 | Wang Q. et al., 1996a |
| G535A[†] | G179S | S2/S3 | 3 | 1 | This |
| A551C | Y184S | S2/S3 | 3 | 2 | This; Jongbloed et al., 1999 |

TABLE 2-continued

Summary of All KVLQT1 Mutations*

| Nucleotide Change[†] | Coding Effect | Position | Exon | Number of families[‡] | Study |
|---|---|---|---|---|---|
| G565A | G189R | S2/S3 | 3 | 3 | Wang Q. et al., 1996a; Jongbloed et al., 1999 |
| insG567–568 | G189fs/94 | S2/S3 | 3 | 1 (RW + JLN) | Splawski et al., 1997b |
| G569A | R190Q | S2/S3 | 3 | 2 | Splawski et al., 1998; Donger et al., 1997 |
| del572–576 | L191fs/90 | S2/S3 | 3 | 1 JLN, 1 RW 2 (JLN + RW) | Tyson et al., 1997; Ackerman et al., 1999b |
| G580C[†] | A194P | S2/S3 | 3 | 1 | This |
| C674T | S225L | S4 | 4 | 2 | This; Priori et al., 1999 |
| G724A | D242N | S4/S5 | 5 | 1 | Itoh et al., 1998b |
| C727T[†] | R243C | S4/S5 | 5 | 2 | This |
| G728A | R243H | S4/S5 | 5 | 1 JLN | Saarinen et al., 1998 |
| T742C[†] | W248R | S4/S5 | 5 | 1 | This |
| T749A | L250H | S4/S5 | 5 | 1 | Itoh et al., 1998a |
| G760A | V254M | S4/S5 | 5 | 4 | This; Wang Q. et al., 1996a; Donger et al., 1997 |
| G781A | E261K | S4/S5 | 6 | 1 | Donger et al., 1997 |
| T797C[†] | L266P | S5 | 6 | 1 | This |
| G805A | G269S | S5 | 6 | 1 | Ackerman et al., 1999b |
| G806A | G269D | S5 | 6 | 3 | This; Donger et al., 1997 |
| C817T | L273F | S5 | 6 | 2 | This; Wang Q. et al., 1996a |
| A842G | Y281C | S5 | 6 | 1 | Priori et al., 1999 |
| G898A | A300T | S5/Pore | 6 | 1 | Priori et al., 1998 |
| G914C | W305S | Pore | 6 | 1 JLN | Chouabe et al., 1997 |
| G916A | G306R | Pore | 6 | 1 | Wang Q. et al, 1996a |
| del921 – (921 + 2) | V307sp | Pore | 6 | 1 | Li et al., 1998 |
| G921 + 1T[†] | V307sp | Pore | 6 | 1 | This |
| A922 – 2C[†] | V307sp | Pore | 7 | 1 | This |
| G922 – 1C | V307sp | Pore | 7 | 1 | Murray et al., 1999 |
| C926G | T309R | Pore | 7 | 1 | Donger et al., 1997 |
| G928A[†] | V310I | Pore | 7 | 1 | This |
| C932T | T311I | Pore | 7 | 1 | Saarinen et al., 1998 |
| C935T | T312I | Pore | 7 | 2 | This; Wang Q. et al., 1996a |
| C939G | I313M | Pore | 7 | 1 | Tanaka et al., 1997 |
| G940A | G314S | Pore | 7 | 7 | Splawski et al., 1998; Russell et al., 1996; Donger et al., 1997; Jongbloed et al., 1999; Itoh et al., 1998b |
| A944C | Y315S | Pore | 7 | 3 | Donger et al., 1997; Jongbloed et al., 1999 |
| A944G | Y315C | Pore | 7 | 2 | Priori et al., 1999; Splawski et al., 1998 |
| G949A | D317N | Pore | 7 | 2 | Wollnik et al., 1997; Saarinen et al., 1998 |
| G954C | K318N | Pore | 7 | 1 | Splawski et al., 1998 |
| C958G | P320A | Pore | 7 | 1 | Donger et al., 1997 |
| G973A | G325R | S6 | 7 | 4 | This; Donger et al., 1997; Tanaka et al., 1997 |
| del1017–1019 | delF340 | S6 | 7 | 2 | This; Ackerman et al., 1998 |
| C1022A | A341E | S6 | 7 | 5 | This; Wang Q. et al., 1996a; Berthet et al., 1999 |
| C1022T | A341V | S6 | 7 | 7 | This; Wang Q. et al., 1996a; Russell et al., 1996; Donger et al., 1997; Li et al., 1998 |
| C1024T | L342F | S6 | 7 | 1 | Donger et al., 1997 |
| C1031T | A344V | S6 | 7 | 1 | Donger et al., 1997 |
| G1032A | A344sp | S6 | 7 | 9 | This; Kanters, 1998; Li et al., 1998; Ackerman et al., 1999b; Murray et al., 1999 |
| G1032C | A344sp | S6 | 7 | 1 | Murray et al., 1999 |
| G1033C | G345R | S6 | 8 | 1 | van den Berg et al., 1997 |
| G1034A | G345E | S6 | 8 | 1 | Wang Q. et al., 1996a |
| C1046G[†] | S349W | S6 | 8 | 1 | This |
| T1058C | L353P | S6 | 8 | 1 | Splawski et al., 1998 |
| C1066T[†] | Q356X | C-terminus | 8 | 1 | This |
| C1096T | R366W | C-terminus | 8 | 1 | Splawski et al., 1998 |
| G1097A[†] | R366Q | C-terminus | 8 | 1 | This |
| G1097C | R366P | C-terminus | 8 | 1 | Tanaka et al., 1997 |
| G1111A | A371T | C-terminus | 8 | 1 | Donger et al., 1997 |

TABLE 2-continued

Summary of All KVLQT1 Mutations*

| Nucleotide Change[†] | Coding Effect | Position | Exon | Number of families[‡] | Study |
|---|---|---|---|---|---|
| T1117C | S373P | C-terminus | 8 | 1 | Jongbloed et al., 1999 |
| C1172T[†] | T391I | C-terminus | 9 | 1 | This |
| T1174C | W392R | C-terminus | 9 | 1 | Jongbloed et al., 1999 |
| C1343G[†] | P448R | C-terminus | 10 | 2 | This |
| C1522T | R518X | C-terminus | 12 | 1 JLN, 3 RW | This; Larsen et al., 1999 |
| G1573A | A525T | C-terminus | 12 | 1 | Larsen et al., 1999b |
| C1588T[†] | Q530X | C-terminus | 12 | 1 JLN, 1 RW | This |
| C1615T | R539W | C-terminus | 13 | 1 | Chouabe et al., 1997 |
| del6/ins7 | E543fs/107 | C-terminus | 13 | 1 JLN | Neyroud et al., 1997 |
| C1663T | R555C | C-terminus | 13 | 3 | Donger et al., 1997 |
| C1697T[†] | S566F | C-terminus | 14 | 3 | This |
| C1747T[†] | R583C | C-terminus | 15 | 1 | This |
| C1760T | T587M | C-terminus | 15 | 1 JLN, 1 RW | Donger et al., 1997; Itoh et al., 1998b |
| G1772A | R591H | C-terminus | 15 | 1 | Donger et al., 1997 |
| G1781A[†] | R594Q | C-terminus | 15 | 3 | This |
| del1892–1911 | P630fs/13 | C-terminus | 16 | 1 JLN | Donger et al., 1997 |
| insC1893–1894 | P631fs/19 | C-terminus | 16 | 1 | Donger et al., 1997 |

*ins denotes insertion; del denotes deletion; sp denotes the last unaffected amino acid before the predicted splice mutation; fs denotes the last amino acid unaffected by a frameshift, following fs is the number of amino acids before termination; X denotes a stop codon occurred.
[†]denotes novel mutation
[‡]Number of Romano-Ward families unless otherwise indicated (UK - unknown)

TABLE 3

Summary of All HERG Mutations*

| Nucleotide Change | Coding Effect | Position | Exon | Number of RW Families | Study |
|---|---|---|---|---|---|
| C87A[†] | F29L | N-terminus | 2 | 1 | This |
| A98C[†] | N33T | N-terminus | 2 | 2 | This |
| C132A[†] | C44X | N-terminus | 2 | 1 | This |
| G140T[†] | G47V | N-terminus | 2 | 1 | This |
| G157C[†] | G53R | N-terminus | 2 | 1 | This |
| G167A[†] | R56Q | N-terminus | 2 | 1 | This |
| T196G[†] | C66G | N-terminus | 2 | 1 | This |
| A209G[†] | H70R | N-terminus | 2 | 2 | This |
| C215A[†] | P72Q | N-terminus | 2 | 2 | This |
| del221–251[†] | R73fs/31 | N-terminus | 2 | 1 | This |
| G232C[†] | A78P | N-terminus | 2 | 1 | This |
| dupl234–250[†] | A83fs/37 | N-terminus | 2 | 1 | This |
| C241T[†] | Q81X | N-terminus | 2 | 1 | This |
| T257G[†] | L86R | N-terminus | 2 | 1 | This |
| insC422–423[†] | P141fs/2 | N-terminus | 3 | 1 | This |
| insC453–454[†] | P151fs/179 | N-terminus | 3 | 1 | This |
| dupl558–600 | L200fs/144 | N-terminus | 4 | 1 | Hoorntje et al., 1999 |
| insC724–725[†] | P241fs/89 | N-terminus | 4 | 1 | This |
| del885[†] | V295fs/63 | N-terminus | 4 | 1 | This |
| C934T[†] | R312C | N-terminus | 5 | 1 | This |
| C1039T[†] | P347S | N-terminus | 5 | 1 | This |
| G1128A[†] | Q376sp | N-terminus | 5 | 1 | This |
| A1129 – 2G[†] | Q376sp | N-terminus | 6 | 1 | This |
| del1261 | Y420fs/12 | S1 | 6 | 1 | Curran et al., 1995 |
| C1283A | S428X | S1/S2 | 6 | 1 | Priori et al., 1999 |
| C1307T | T436M | S1/S2 | 6 | 1 | Priori et al., 1999 |
| A1408G | N470D | S2 | 6 | 1 | Curran et al., 1995 |
| C1421T | T474I | S2/S3 | 6 | 1 | Tanaka et al., 1997 |
| C1479G | Y493X | S2/S3 | 6 | 1 | Itoh et al., 1998a |
| del1498–1524 | del500 –508 | S3 | 6 | 1 | Curran et al., 1995 |
| G1592A[†] | R531Q | S4 | 7 | 1 | This |
| C1600T | R534C | S4 | 7 | 1 | Itoh et al., 1998a |
| T1655C[†] | L552S | S5 | 7 | 1 | This |
| delT1671 | T556fs/7 | S5 | 7 | 1 | Schulze-Bahr et al., 1995 |
| G1672C | A558P | S5 | 7 | 1 | Jongbloed et al., 1999 |
| G1681A | A561T | S5 | 7 | 4 | This; Dausse et al., 1996 |
| C1682T | A561V | S5 | 7 | 4 | This; Curran et al., 1995; Priori et al., 1999 |

TABLE 3-continued

Summary of All HERG Mutations*

| Nucleotide Change | Coding Effect | Position | Exon | Number of RW Families | Study |
|---|---|---|---|---|---|
| G1714C | G572R | S5/Pore | 7 | 1 | Larsen et al., 1999a |
| G1714T | G572C | S5/Pore | 7 | 1 | Splawski et al., 1998 |
| C1744T | R582C | S5/Pore | 7 | 1 | Jongbloed et al., 1999 |
| G1750A† | G584S | S5/Pore | 7 | 1 | This |
| G1755T† | W585C | S5/Pore | 7 | 1 | This |
| A1762G | N588D | S5/Pore | 7 | 1 | Splawski et al., 1998 |
| T1778C† | I593T | S5/Pore | 7 | 1 | This |
| T1778G | I593R | S5/Pore | 7 | 1 | Benson et al., 1996 |
| G1801A | G601S | S5/Pore | 7 | 1 | Akimoto et al., 1998 |
| G1810A | G604S | S5/Pore | 7 | 2 | This; Jongbloed et al., 1999 |
| G1825A† | D609N | S5/Pore | 7 | 1 | This |
| T1831C | Y611H | S5/Pore | 7 | 1 | Tanaka et al., 1997 |
| T1833 (A or G) | Y611X | S5/Pore | 7 | 1 | Schulze-Bahr et al., 1995 |
| G1834T | V612L | Pore | 7 | 1 | Satler et al., 1998 |
| C1838T | T613M | Pore | 7 | 4 | This; Jongbloed et al., 1999 |
| C1841T | A614V | Pore | 7 | 6 | Priori et al., 1999; Splawski et al., 1998; Tanaka et al., 1997; Satler et al., 1998 |
| C1843G† | L615V | Pore | 7 | 1 | This |
| G1876A† | G626S | Pore | 7 | 1 | This |
| C1881G† | F627L | Pore | 7 | 1 | This |
| G1882A | G628S | Pore | 7 | 2 | This; Curran et al., 1995 |
| A1885G | N629D | Pore | 7 | 1 | Satler et al., 1998 |
| A1886G | N629S | Pore | 7 | 1 | Satler et al., 1998 |
| C1887A | N629K | Pore | 7 | 1 | Yoshida et al., 1999 |
| G1888C | V630L | Pore | 7 | 1 | Tanaka et al., 1997 |
| T1889C | V630A | Pore | 7 | 1 | Splawski et al., 1998 |
| C1894T† | P632S | Pore | 7 | 1 | This |
| A1898G | N633S | Pore | 7 | 1 | Satler et al., 1998 |
| A1912G† | K638E | S6 | 7 | 1 | This |
| del1913–1915† | delK638 | S6 | 7 | 1 | This |
| C1920A | F640L | S6 | 7 | 1 | Jongbloed et al., 1999 |
| A1933T† | M645L | S6 | 7 | 1 | This |
| del1951–1952 | L650fs/2 | S6 | 8 | 1 | Itoh et al., 1998a |
| G2044T† | E682X | S6/cNBD | 8 | 1 | This |
| C2173T | Q725X | S6/cNBD | 9 | 1 | Itoh et al., 1998a |
| insT2218–2219† | H739fs/63 | S6/cNBD | 9 | 1 | This |
| C2254T† | R752W | S6/cNBD | 9 | 1 | This |
| dupl2356–2386 | V796fs/22 | cNBD | 9 | 1 | Itoh et al., 1998a |
| del2395† | I798fs/10 | cNBD | 9 | 1 | This |
| G2398 + 1C | L799sp | cNBD | 9 | 2 | This; Curran et al., 1995 |
| T2414C† | F805S | cNBD | 10 | 1 | This |
| T2414G† | F805C | cNBD | 10 | 1 | This |
| C2453T | S818L | cNBD | 10 | 1 | Berthet et al., 1999 |
| G2464A | V822M | cNBD | 10 | 2 | Berthet et al., 1999; Satler et al., 1996 |
| C2467T† | R823W | cNBD | 10 | 2 | This |
| A2582T† | N861I | C-terminus | 10 | 1 | This |
| G2592 + 1A | D864sp | C-terminus | 10 | 2 | This; Berthet et al., 1999 |
| del2660† | K886fs/85 | C-terminus | 11 | 1 | This |
| C2750T† | P917L | C-terminus | 12 | 1 | This |
| del2762† | R920fs/51 | C-terminus | 12 | 1 | This |
| C2764T† | R922W | C-terminus | 12 | 1 | This |
| insG2775–2776† | G925fs/13 | C-terminus | 12 | 1 | This |
| del2906† | P968fs/4 | C-terminus | 12 | 1 | This |
| del2959–2960† | P986fs/130 | C-terminus | 12 | 1 | This |
| C3040T† | R1014X | C-terminus | 13 | 2 | This |
| del3094† | G1031fs/24 | C-terminus | 13 | 1 | This |
| insG3107–3108 | G1036fs/82 | C-terminus | 13 | 1 | Berthet et al., 1999 |
| insC3303–3304† | P1101fs | C-terminus | 14 | 1 | This |

*all characters same as in Table 2

TABLE 4

Summary of All SCN5A Mutations

| Nucleotide Change | Coding Effect | Position | Exon | Number of RW Families | Study |
|---|---|---|---|---|---|
| G3340A† | D1114N | DII/DIII | 18 | 1 | This |
| C3911T | T1304M | DIII/S4 | 22 | 1 | Wattanasirichaigoon et al., 1999 |
| A3974G | N1325S | DIII/S4/S5 | 23 | 1 | Wang et al., 1995b |
| C4501G† | L1501V | DIII/DIV | 26 | 1 | This |
| del4511–4519 | del1505–1507 | DIII/DIV | 26 | 4 | Wang et al., 1995a; Wang et al., 1995b |
| del4850–4852† | delF1617 | DIV/S3/S4 | 28 | 1 | This |
| G4868A | R1623Q | DIV/S4 | 28 | 2 | This; Makita et al., 1998 |
| G4868T† | R1623L | DIV/S4 | 28 | 1 | This |
| G4931A | R1644H | DIV/S4 | 28 | 2 | This; Wang et al., 1995b |
| C4934T | T1645M | DIV/S4 | 28 | 1 | Wattanasirichaigoon et al., 1999 |
| G5350A† | E1784K | C-terminus | 28 | 2 | This; Wei et al., 1999 |
| G5360A† | S1787N | C-terminus | 28 | 1 | This |
| A5369G | D1790G | C-terminus | 28 | 1 | An et al., 1998 |
| insTGA 5385–5386 | insD1795–1796 | C-terminus | 28 | 1 | Bezzina et al., 1999 |

*all characters same as in Table 2. Fifty individuals with suspected abnormalities in $I_{Na}$ were screened for all SCN5A exons. All individuals were screened for exons 23–28.

TABLE 5

Summary of All KCNE1 Mutations*

| Nucleotide Change | Coding Effect | Position | Exon | Number of Families | Study |
|---|---|---|---|---|---|
| C20T | T71 | N-terminus | 3 | 1 JLN | Schulze-Bahr et al., 1997 |
| G95A† | R32H | N-terminus | 3 | 1 | This |
| G139T | V47F | S1 | 3 | 1 JLN | Bianchi et al., 1999 |
| TG151–152AT | L51H | S1 | 3 | 1 JLN | Bianchi et al., 1999 |
| A172C/TG176–177CT | TL58–59PP | S1 | 3 | 1 JLN | Tyson et al., 1997 |
| C221T | S74L | C-terminus | 3 | 1 | Splawski et al., 1997a |
| G226A | D76N | C-terminus | 3 | 1 JLN, 1 RW, 1 (JLN + RW) | Splawski et al., 1997a; Tyson et al., 1997; Duggal et al., 1998 |
| T259C | W87R | C-terminus | 3 | 1 | Bianchi et al., 1999 |
| C292T† | R98W | C-terminus | 3 | 1 | This |
| C379A† | P127T | C-terminus | 3 | 1 | This |

*all characters same as in Table 2

TABLE 6

Summary of All KCNE2 Mutations

| Nucleotide Change | Coding Effect | Position | Exon | Number of Families | Study |
|---|---|---|---|---|---|
| C25G | Q9E | N-terminus | 1 | 1 | Abbott et al., 1999 |
| T161T | M54T | S1 | 1 | 1 | Abbott et al., 1999 |
| T170C | I57T | S1 | 1 | 1 | Abbott et al., 1999 |

TABLE 7

Mutations by Type

| Type | KVLQT1 | HERG | SCN5A | KCNE1 | KCNE2 | Total |
|---|---|---|---|---|---|---|
| Missense | 59 | 52 | 9 | 5 | 3 | 128 |
| Nonsense | 6 | 5 | 0 | 0 | 0 | 11 |
| AA deletion* | 2 | 2 | 5 | 0 | 0 | 9 |
| Frameshift | 1 | 16 | 0 | 0 | 0 | 17 |
| Splice | 7 | 5 | 0 | 0 | 0 | 12 |
| Total | 75 | 80 | 14 | 5 | 3 | 177 |

*AA denotes amino acid

TABLE 8

Mutations by Position

| Gene Protein Position | KVLQT1 KVLQT1 | HERG HERG | SCN5A SCN5A | KCNE1 minK | KCNE2 MiRP1 | Total |
|---|---|---|---|---|---|---|
| Extracellular | 0 | 7 | 1 | 1 | 1 | 10 |
| Transmembrane | 33 | 13 | 5 | 0 | 2 | 53 |
| Pore | 9 | 12 | 0 | N/A | N/A | 21 |
| Intracellular | 33 | 48 | 8 | 4 | 0 | 93 |
| Total | 75 | 80 | 14 | 5 | 3 | 177 |

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Abbott G W, et al. (1999). *Cell* 97:175–187.
Ackerman M J, et al. (1998). *Pediatr. Res.* 44:148–153.
Ackerman M J, et al. (1999a). *N. Engl. J. Med.* 341:1121–1125.
Ackerman M J, et al. (1999b). *Mayo Clin. Proc.* 74:1088–1094.
Akimoto K, et al. (1998). *Hum. Mutat.* 1:S184–S186.
An R H, et al. (1998). *Circ. Res.* 83:141–146.
Ausubel F M, et al. (1992). *Current Protocols in Molecular Biology*, (John Wiley and Sons, New York, N.Y.).
Barhanin J, et al. (1996). *Nature* 384:78–80.
Beaucage S L, and Caruthers M H (1981). *Tetra. Letts.* 22:1859–1862.
Bennett P B, et al. (1995). *Nature* 376:683–685.
Benson D W, et al. (1996). *Circulation* 93: 1791–1795.
Berthet M, et al. (1999). *Circulation* 99:1464–1470.
Bezzina C, et al. (1999). *Circ. Res.* 85:1206–1213.
Bianchi L, et al. (1999). *Hum. Mol. Genet.* 8:1499–1507.
Borman S (1996). *Chemical & Engineering News*, December 9 issue, pp. 42–43.
Cariello N F (1988). *Am. J. Human Genetics* 42:726–734.
Chee M, et al. (1996). *Science* 274:610–614.
Chen J, et al. (1999). *J. Biol. Chem.* 274:10113–10118.
Chen Q, et al. (1999). *Circulation* 99:1344–1347.
Chouabe C, et al. (1997). *EMBO J.* 16:5472–5479.
Compton S J, et al. (1996). *Circulation* 94:1018–1022.
Conner B J, et al. (1983). *Proc. Natl. Acad. Sci. USA* 80:278–282.
Cotton R G, et al. (1988). *Proc. Natl. Acad. Sci. USA* 85:4397–4401.
Curran M E, et al. (1995). *Cell* 80:795–803.
Dausse E, et al. (1996). *J. Mol. Cell. Cardiol.* 28:1609–1615.
DeRisi J, et al. (1996). *Nat. Genet.* 14:457–460.
Donger C, et al. (1997). *Circulation* 96:2778–2781.
Doyle D A, et al. (1998). *Science* 280:69–77.
Duggal P, et al. (1998). *Circulation* 97:142–146.
Dumaine R, et al. (1996). *Circ. Res.* 78:914–924.
Editorial (1996). *Nature Genetics* 14:367–370.
Elghanian R, et al. (1997). *Science* 277:1078–1081.
*Enhancers and Eukaryotic Gene Expression*, Cold Spring Harbor Press, Cold Spring, Harbor, N.Y. (1983).
Fiers W, et al. (1978). *Nature* 273:113–120.
Finkelstein J, et al. (1990). *Genomics* 7:167–172.
Fodor S P A (1997). *Science* 277:393–395.
Franqueza L, et al. (1999). *J. Biol. Chem.* 274:21063–21070.
Furutani M, et al. (1999). *Circulation* 99:2290–2294.
Gellens M, et al. (1992). *Proc. Natl. Acad. Sci. USA* 89:554–558.
Grompe M (1993). *Nature Genetics* 5:111–117.
Grompe M, et al., (1989). *Proc. Natl. Acad. Sci. USA* 86:5855–5892.
Hacia J G, et al. (1996). *Nature Genetics* 14:441–447.
Hoorntje T, et al. (1999). *Circulation* 100:1264–1267.
Itoh T, et al. (1998a). *Hum. Genet.* 102:435–439.
Itoh T, et al. (1998b). *Hum. Genet.* 103:290–294.
Jakoby W B and Pastan I H (eds.) (1979). Cell Culture. *Methods in Enzymology* volume 58 (Academic Press, Inc., Harcourt Brace Jovanovich (New York)).
Jervell A and Lange-Nielsen F (1957). *Am. Heart J.* 54:59–68.
Jiang C, et al. (1994). *Nat. Genet.* 8:141–147.
Jongbloed R J, et al. (1999). *Hum. Mutat.* 13:301–310.
Kanters J (1998). *J. Cardiovasc. Electrolphysiol.* 9:620–624.
Keating M, et al. (1991). *Science* 252:704–706.
Kinszler K W, et al. (1991). *Science* 251:1366–1370.
Kubo T, et al. (1988). *FEBS Lett.* 241:119.
Larsen L A, et al. (1999a). *Hum. Mutat.* 13:318–327.
Larsen L A, et al. (1999b). *Eur. J. Hum. Genet.* 7:724–728.
Li H, et al. (1998). *Circulation* 97:1264–1269.
Lipshutz R J, et al. (1995). *Biotechniques* 19:442–447.
Lockhart D J, et al. (1996). *Nature Biotechnology* 14:1675–1680.
Ludwig J, et al. (1994). *EMBO J.* 13:4451–4458.
MacKinnon R, et al. (1998). *Science* 280:106–109.
Makita N, et al. (1998). *FEBS Lett.* 423:5–9.
Matteucci M D and Caruthers M H (1981). *J. Am. Chem. Soc.* 103:3185.
Metzger D, et al. (1988). *Nature* 334:31–36.
Modrich P (1991). *Ann. Rev. Genet.* 25:229–253.
Mohammad-Panah R, et al. (1999). *Am. J. Hum. Genet.* 64:1015–1023.
Moss A, et al. (1991). *Circulation* 84:1136–1144.
Murray A, et al. (1999). *Circulation* 100:1077–1084.
Newton C R, et al. (1989). *Nucl. Acids Res.* 17:2503–2516.
Neyroud N, et al. (1997). *Nat. Genet.* 15:186–189.
Neyroud N, et al. (1998). *Eur. J. Hum. Genet.* 6:129–133.
Neyroud N, et al. (1999). *Circ. Res.* 84:290–297.
Novack D F, et al. (1986). *Proc. Natl. Acad. Sci. USA* 83:586–590.
Orita M, et al. (1989). *Proc. Natl. Acad. Sci. USA* 86:2766–2770.
Priori S G, et al. (1998). *Circulation* 97:2420–2425.
Priori S G, et al. (1999). *Circulation* 99:529–533.
Romano C, et al. (1963). *Clin. Pediatr.* 45:656–683.
Ruano G and Kidd K K (1989). *Nucl. Acids Res.* 17:8392.
Russell M W, et al. (1996). *Hum. Mol. Genet.* 5:1319–1324.
Saarinen K, et al. (1998). *Hum. Mutat.* 11:158–165.
Sambrook J, et al. (1989). *Molecular Cloning: A Laboratory Manual*, 2nd Ed. (Cold Spring Harbor Laboratory, Cold Spring Harbor, N.Y.).
Sanguinetti M C, et al. (1996a). *Nature* 384:80–83.
Sanguinetti M C, et al. (1996b). *Proc. Natl. Acad. Sci. USA* 93:2208–2212.
Satler C A, et al. (1996). *Am. J. Med. Genet.* 65:27–35.
Satler C A, et al. (1998). *Hum. Genet.* 102:265–272.
Schott J, et al. (1995). *Am. J. Hum. Genet.* 57:1114–1122.
Schulze-Bahr E, et al. (1995). *N. Engl. J. Med.* 333:1783–1784.
Schulze-Bahr E, et al. (1997). *Nat. Genet.* 17:267–268.
Schwartz P J, et al. (1975). *Am. Heart J.* 89:378–390.

Schwartz P J, et al. (1995). *Circulation* 92:3381–3386.
Sesti F and Goldstein S A (1998). *J. Gen. Physiol.* 112:651–663.
Shalaby F Y, et al. (1997). *Circulation* 96:1733–1736.
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1 975). *Proc. Natl. Acad. Sci. USA* 72:989–993.
Shoemaker D D, et al. (1 996). *Nature Genetics* 14:450–456.
Splawski I, et al. (1997a). *Nat. Genet.* 17:338–340.
Splawski I, et al. (1997b). *N. Engl. J. Med.* 336:1562–1567.
Splawski I, et al. (1998). *Genomics* 51:86–97.
Tanaka T, et al. (1997). *Circulation* 95:565–567.
Tyson J, et al. (1997). *Hum. Mol. Genet.* 6:2179–2185.
van den Berg M H, et al. (1997). *Hum. Genet.* 100:356–361.
Vetter D E, et al. (1996). *Neuron* 17:1251–1264.
Vincent G M, et al. (1992). *N. Engl. J. Med.* 327:846–852.
Wang D W (1996). *Proc. Natl. Acad. Sci. USA* 93:13200–13205.
Wang Q, et al. (1995a). *Cell* 80:805–811.
Wang Q, et al. (1995b). *Hum. Mol. Genet.* 4:1603–1607.
Wang Q, et al. (1996a). *Nat. Genet.* 12:17–23.
Wang Q, et al. (1996b). *Genomics* 34:9–16.
Wang Z, et al. (1999). *J. Cardiovasc. Electrophysiol.* 10:817–826.
Ward O C (1964). *J. Ir. Med. Assoc.* 54:103–106.
Wartell R M, et al. (1990). *Nucl. Acids Res.* 18:2699–2705.
Wattanasirichaigoon D, et al. (1999). *Am. J. Med. Genet.* 86:470–476.
Wei J, et al. (1999). *Circulation* 99:3165–3171.
White M B, et al. (1992). *Genomics* 12:301–306.
Wollnik B, et al. (1997). *Hum. Mol. Genet.* 6:1943–1949.
Yoshida H, et al. (1999). *J. Cardiovasc. Electrophysiol.* 10:1262–1270.
Zhou Z, et al. (1998). *J. Biol. Chemi.* 273:21061–21066.
Hitzeman et al., EP 73,675A.
European Patent Application Publication No. 0332435.
U.S. Pat. No. 5,436,146
U.S. Pat. No. 5,691,198
U.S. Pat. No. 5,735,500
U.S. Pat. No. 5,747,469

What is claimed:

1. An isolated DNA comprising a sequence of SEQ ID NO:1 as altered by one or more mutations selected from the group consisting of A332G, G478A, G521A, G535A, G580C and C727T.

2. A nucleic acid probe specifically hybridizable to a human mutated KVLQT1 and not to wild-type DNA, said mutated KVLQT1 comprising a mutation of SEQ ID NO:1 selected from the group consisting of A332G, G478A, G521A, G535A, G580C and C727T.

3. A method for detecting a mutation in KVLQT1 said mutation selected from the group consisting of A332G, G478A, G521A, G535A, G580C and C727T which comprises analyzing a sequence of said KVLQT1 or KVLQT1 RNA from a human sample or analyzing the sequence of cDNA made from mRNA from said sample.

4. The method of claim 3 wherein said mutation is detected by a method selected from the group consisting of:
   a) hybridizing a probe specific for one of said mutations to RNA isolated from said human sample and detecting the presence of a hybridization product, wherein the presence of said product indicates the presence of said mutation in the sample;

b) hybridizing a probe specific for one of said mutations to cDNA made from RNA isolated from said sample and detecting the presence of a hybridization product, wherein the presence of said product indicates the presence of said mutation in the sample;

c) hybridizing a probe specific for one of said mutations to genomic DNA isolated from said sample and detecting the presence of a hybridization product, wherein the presence of said product indicates the presence of said mutation in the sample;

d) amplifying all or part of said KVLQT1 in said sample using a set of primers to produce amplified nucleic acids and sequencing the amplified nucleic acids;

e) amplifying part of said KVLQT1 in said sample using a primer specific for one of said mutations and detecting the presence of an amplified product, wherein the presence of said product indicates the presence of said mutation in the sample;

f) molecularly cloning all or part of said KVLQT1 in said sample to produce a cloned nucleic acid and sequencing the cloned nucleic acid;

g) amplifying said KVLQT1 to produce amplified nucleic acids, hybridizing the amplified nucleic acids to a DNA probe specific for one of said mutations and detecting the presence of a hybridization product, wherein the presence of said product indicates the presence of said mutation;

h) forming single-stranded DNA from a KVLQT1 fragment of said gene from said human sample and single-stranded DNA from a corresponding fragment of a wild-type KVLQT1, electrophoresing said single-stranded DNAs on a non-denaturing polyacrylamide gel and comparing the mobility of said single-stranded DNAs on said gel to determine if said single-stranded DNA from said sample is shifted relative to wild-type and sequencing said single-stranded DNA having a shift in mobility;

i) forming a heteroduplex consisting of a first strand of nucleic acid selected from the group consisting of a genomic DNA fragment isolated from said sample, an RNA fragment isolated from said sample and a cDNA fragment made from mRNA from said sample and a second strand of a nucleic acid consisting of a corresponding human wild-type gene fragment, analyzing for the presence of a mismatch in said heteroduplex, and sequencing said first strand of nucleic acid having a mismatch;

j) forming single-stranded DNA from said KVLQT1 of said human sample and from a corresponding fragment of an allele specific for one of said mutations, electrophoresing said single-stranded DNAs on a non-denaturing polyacrylamide gel and comparing the mobility of said single-stranded DNAs on said gel to determine if said single-stranded DNA from said sample is shifted relative to said allele, wherein no shift in electrophoretic mobility of the single-stranded DNA relative to the allele indicates the presence of said mutation in said sample; and k) forming a heteroduplex consisting of a first strand of nucleic acid selected from the group consisting of a genomic DNA fragment of said KVLQT1 isolated from said sample, an RNA fragment isolated from said sample and a cDNA fragment made from mRNA from said sample and a second strand of a nucleic acid consisting of a corresponding gene allele fragment specific for one of said mutations and analyzing for the presence of a mismatch in said heteroduplex, wherein no mismatch indicates the presence of said mutation.

5. A method according to claim 4 wherein hybridization is performed in situ.

6. A method of assessing a risk in a human subject for long QT syndrome which comprises screening said subject for a mutation in KVLQT1 by comparing the sequence of said KVLQT1 or its expression products isolated from a tissue sample of said subject with a wild-type sequence of said KVLQT1 or its expression products, wherein said mutation is selected from the group consisting of A332G, G478A, G521A, G535A, G580C and C727T and wherein a mutation in the sequence of the subject indicates a risk for long QT syndrome.

7. The method of claim 6 wherein said expression product is selected from mRNA of said KVLQT1 or a polypeptide encoded by said gene KVLQT1.

8. The method of claim 6 wherein one or more of the following procedures is carried out:

(a) observing shifts in electrophoretic mobility of single-stranded DNA from said sample on non-denaturing polyacrylamide gels;

(b) hybridizing a probe to genomic DNA isolated from said sample under conditions suitable for hybridization of said probe to said KVLQT1;

(c) determining hybridization of an allele-specific probe to genomic DNA from said sample;

(d) amplifying all or part of said KVLQT1 from said sample to produce an amplified sequence and sequencing the amplified sequence;

(e) determining by nucleic acid amplification the presence of a specific mutant allele in said sample;

(f) molecularly cloning all or part of said KVLQT1 from said sample to produce a cloned sequence and sequencing the cloned sequence;

(g) determining whether there is a mismatch between molecules (1) said KVLQT1 genomic DNA or mRNA isolated from said sample, and (2) a nucleic acid probe complementary to the human wild-type KVLQT1 DNA, when molecules (1) and (2) are hybridized to each other to form a duplex;

(h) amplification of said KVLQT1 sequences in said sample and hybridization of the amplified sequences to nucleic acid probes which comprise wild-type gene sequences;

(i) amplification of said KVLQT1 sequences in said tissue and hybridization of the amplified sequences to nucleic acid probes which comprise said mutant KVLQT1 sequences;

(j) screening for a deletion mutation;

(k) screening for a point mutation;

(l) screening for an insertion mutation;

(m) determining in situ hybridization of said KVLQT1 in said sample with one or more nucleic acid probes which comprise said KVLQT1 sequence or a mutant sequence of said KVLQT1;

(n) immunoblotting;

(o) immunocytochemistry;

(p) assaying for binding interactions between said a KVLQT1 polypeptide isolated from said tissue and a binding partner capable of specifically binding the polypeptide expression product of a mutant allele and/or a binding partner for the polypeptide; and (q) assaying for the inhibition of biochemical activity of said binding partner.

9. A nucleic acid probe which hybridizes to the isolated DNA of claim 1 under conditions at which it will not hybridize to wild-type DNA.

10. A method for diagnosing a mutation which causes long QT syndrome comprising hybridizing a probe of claim 9 to a patient's sample of DNA or RNA, the presence of a hybridization signal being indicative of long QT syndrome.

11. A method according to claim 10 wherein the patient's DNA or RNA has been amplified and said amplified DNA or RNA is hybridized with a probe of claim 9.

12. A method according to claim 10 wherein said hybridization is performed in situ.

13. A method according to claim 10 wherein said method is performed using nucleic acid microchip technology.

14. A method for diagnosing a mutation which causes long QT syndrome comprising amplifying a region of the gene or RNA for KVLQT1 and sequencing the amplified gene or RNA wherein long QT syndrome is indicated by any one or more mutations selected from the group consisting of A332G, G478A, G521A, G535A, G580C and C727T.

15. A method for diagnosing a mutation which causes long QT syndrome comprising identifying a mismatch between a patient's DNA or RNA and a wild-type DNA or RNA probe wherein said probe hybridizes to a region of DNA or RNA wherein said region comprises a mutation of SEQ ID NO:1 selected from the group consisting of A332G, G478A, G521A, G535A, G580C and C727T.

16. The method of claim 15 wherein the mismatch is identified by an RNase assay.

17. An isolated DNA encoding a KVLQT1 polypeptide of SEQ ID NO:2 having a mutation selected from the group consisting of Y111C, E160K, R174H, G179S, A194P, and R243C.

* * * * *

SEQUENCE LISTING

<160> NUMBER OF SEQ ID NOS: 4

<210> SEQ ID NO 1
<211> LENGTH: 2028
<212> TYPE: DNA
<213> ORGANISM: Homo sapiens
<220> FEATURE:
<221> NAME/KEY: CDS
<222> LOCATION: (1)..(2028)

<400> SEQUENCE: 1

```
atg gcc gcg gcc tcc tcc ccg ccc agg gcc gag agg aag cgc tgg ggt       48
Met Ala Ala Ala Ser Ser Pro Pro Arg Ala Glu Arg Lys Arg Trp Gly
 1               5                  10                  15 tgg ggc cgc ctg cca ggc gcc cgg cgg ggc agc gcg ggc ctg gcc aag       96
Trp Gly Arg Leu Pro Gly Ala Arg Arg Gly Ser Ala Gly Leu Ala Lys
             20                  25                  30 aag tgc ccc ttc tcg ctg gag ctg gcg gag ggc ggc ccg gcg ggc ggc      144
Lys Cys Pro Phe Ser Leu Glu Leu Ala Glu Gly Gly Pro Ala Gly Gly
         35                  40                  45 gcg ctc tac gcg ccc atc gcg ccc ggc gcc cca ggt ccc gcg ccc cct      192
Ala Leu Tyr Ala Pro Ile Ala Pro Gly Ala Pro Gly Pro Ala Pro Pro
     50                  55                  60 gcg tcc ccg gcc gcg ccc gcc gcg ccc cca gtt gcc tcc gac ctt ggc      240
Ala Ser Pro Ala Ala Pro Ala Ala Pro Pro Val Ala Ser Asp Leu Gly
 65                  70                  75                  80 ccg cgg ccg ccg gtg agc cta gac ccg cgc gtc tcc atc tac agc acg      288
Pro Arg Pro Pro Val Ser Leu Asp Pro Arg Val Ser Ile Tyr Ser Thr
                 85                  90                  95 cgc cgc ccg gtg ttg gcg cgc acc cac gtc cag ggc cgc gtc tac aac      336
Arg Arg Pro Val Leu Ala Arg Thr His Val Gln Gly Arg Val Tyr Asn
            100                 105                 110 ttc ctc gag cgt ccc acc ggc tgg aaa tgc ttc gtt tac cac ttc gcc      384
Phe Leu Glu Arg Pro Thr Gly Trp Lys Cys Phe Val Tyr His Phe Ala
        115                 120                 125 gtc ttc ctc atc gtc ctg gtc tgc ctc atc ttc agc gtg ctg tcc acc      432
Val Phe Leu Ile Val Leu Val Cys Leu Ile Phe Ser Val Leu Ser Thr
    130                 135                 140 atc gag cag tat gcc gcc ctg gcc acg ggg act ctc ttc tgg atg gag      480
Ile Glu Gln Tyr Ala Ala Leu Ala Thr Gly Thr Leu Phe Trp Met Glu
```

| | | | | | | | | | | | | | | | |
|---|---|---|---|---|---|---|---|---|---|---|---|---|---|---|---|
|Ile|Glu|Gln|Tyr|Ala|Ala|Leu|Ala|Thr|Gly|Thr|Leu|Phe|Trp|Met|Glu|
|145| | | |150| | | |155| | | |160| | | |

```
atc gtg ctg gtg gtg ttc ttc ggg acg gag tac gtg gtc cgc ctc tgg      528
Ile Val Leu Val Val Phe Phe Gly Thr Glu Tyr Val Val Arg Leu Trp
            165             170             175 tcc gcc ggc tgc cgc agc aag tac gtg ggc ctc tgg ggg cgg ctg cgc      576
Ser Ala Gly Cys Arg Ser Lys Tyr Val Gly Leu Trp Gly Arg Leu Arg
        180             185             190 ttt gcc cgg aag ccc att tcc atc atc gac ctc atc gtg gtc gtg gcc      624
Phe Ala Arg Lys Pro Ile Ser Ile Ile Asp Leu Ile Val Val Val Ala
        195             200             205 tcc atg gtg gtc ctc tgc gtg ggc tcc aag ggg cag gtg ttt gcc acg      672
Ser Met Val Val Leu Cys Val Gly Ser Lys Gly Gln Val Phe Ala Thr
    210             215             220 tcg gcc atc agg ggc atc cgc ttc ctg cag atc ctg agg atg cta cac      720
Ser Ala Ile Arg Gly Ile Arg Phe Leu Gln Ile Leu Arg Met Leu His
225             230             235             240 gtc gac cgc cag gga ggc acc tgg agg ctc ctg ggc tcc gtg gtc ttc      768
Val Asp Arg Gln Gly Gly Thr Trp Arg Leu Leu Gly Ser Val Val Phe
            245             250             255 atc cac cgc cag gag ctg ata acc acc ctg tac atc ggc ttc ctg ggc      816
Ile His Arg Gln Glu Leu Ile Thr Thr Leu Tyr Ile Gly Phe Leu Gly
        260             265             270 ctc atc ttc tcc tcg tac ttt gtg tac ctg gct gag aag gac gcg gtg      864
Leu Ile Phe Ser Ser Tyr Phe Val Tyr Leu Ala Glu Lys Asp Ala Val
        275             280             285 aac gag tca ggc cgc gtg gag ttc ggc agc tac gca gat gcg ctg tgg      912
Asn Glu Ser Gly Arg Val Glu Phe Gly Ser Tyr Ala Asp Ala Leu Trp
    290             295             300 tgg ggg gtg gtc aca gtc acc acc atc ggc tat ggg gac aag gtg ccc      960
Trp Gly Val Val Thr Val Thr Thr Ile Gly Tyr Gly Asp Lys Val Pro
305             310             315             320 cag acg tgg gtc ggg aag acc atc gcc tcc tgc ttc tct gtc ttt gcc     1008
Gln Thr Trp Val Gly Lys Thr Ile Ala Ser Cys Phe Ser Val Phe Ala
            325             330             335 atc tcc ttc ttt gcg ctc cca gcg ggg att ctt ggc tcg ggg ttt gcc     1056
Ile Ser Phe Phe Ala Leu Pro Ala Gly Ile Leu Gly Ser Gly Phe Ala
        340             345             350 ctg aag gtg cag cag aag cag agg cag aag cac ttc aac cgg cag atc     1104
Leu Lys Val Gln Gln Lys Gln Arg Gln Lys His Phe Asn Arg Gln Ile
        355             360             365 ccg gcg gca gcc tca ctc att cag acc gca tgg agg tgc tat gct gcc     1152
Pro Ala Ala Ala Ser Leu Ile Gln Thr Ala Trp Arg Cys Tyr Ala Ala
370             375             380 gag aac ccc gac tcc tcc acc tgg aag atc tac atc cgg aag gcc ccc     1200
Glu Asn Pro Asp Ser Ser Thr Trp Lys Ile Tyr Ile Arg Lys Ala Pro
385             390             395             400 cgg agc cac act ctg ctg tca ccc agc ccc aaa ccc aag aag tct gtg     1248
Arg Ser His Thr Leu Leu Ser Pro Ser Pro Lys Pro Lys Lys Ser Val
            405             410             415 gtg gta aag aaa aaa aag ttc aag ctg gac aaa gac aat ggg gtg act     1296
Val Val Lys Lys Lys Lys Phe Lys Leu Asp Lys Asp Asn Gly Val Thr
        420             425             430 cct gga gag aag atg ctc aca gtc ccc cat atc acg tgc gac ccc cca     1344
Pro Gly Glu Lys Met Leu Thr Val Pro His Ile Thr Cys Asp Pro Pro
        435             440             445 gaa gag cgg cgg ctg gac cac ttc tct gtc gac ggc tat gac agt tct     1392
Glu Glu Arg Arg Leu Asp His Phe Ser Val Asp Gly Tyr Asp Ser Ser
450             455             460
```

```
gta agg aag agc cca aca ctg ctg gaa gtg agc atg ccc cat ttc atg        1440
Val Arg Lys Ser Pro Thr Leu Leu Glu Val Ser Met Pro His Phe Met
465                 470                 475                 480 aga acc aac agc ttc gcc gag gac ctg gac ctg gaa ggg gag act ctg        1488
Arg Thr Asn Ser Phe Ala Glu Asp Leu Asp Leu Glu Gly Glu Thr Leu
                485                 490                 495 ctg aca ccc atc acc cac atc tca cag ctg cgg gaa cac cat cgg gcc        1536
Leu Thr Pro Ile Thr His Ile Ser Gln Leu Arg Glu His His Arg Ala
            500                 505                 510 acc att aag gtc att cga cgc atg cag tac ttt gtg gcc aag aag aaa        1584
Thr Ile Lys Val Ile Arg Arg Met Gln Tyr Phe Val Ala Lys Lys Lys
        515                 520                 525 ttc cag caa gcg cgg aag cct tac gat gtg cgg gac gtc att gag cag        1632
Phe Gln Gln Ala Arg Lys Pro Tyr Asp Val Arg Asp Val Ile Glu Gln
530                 535                 540 tac tcg cag ggc cac ctc aac ctc atg gtg cgc atc aag gag ctg cag        1680
Tyr Ser Gln Gly His Leu Asn Leu Met Val Arg Ile Lys Glu Leu Gln
545                 550                 555                 560 agg agg ctg gac cag tcc att ggg aag ccc tca ctg ttc atc tcc gtc        1728
Arg Arg Leu Asp Gln Ser Ile Gly Lys Pro Ser Leu Phe Ile Ser Val
                565                 570                 575 tca gaa aag agc aag gat cgc ggc agc aac acg atc ggc gcc cgc ctg        1776
Ser Glu Lys Ser Lys Asp Arg Gly Ser Asn Thr Ile Gly Ala Arg Leu
            580                 585                 590 aac cga gta gaa gac aag gtg acg cag ctg gac cag agg ctg gca ctc        1824
Asn Arg Val Glu Asp Lys Val Thr Gln Leu Asp Gln Arg Leu Ala Leu
        595                 600                 605 atc acc gac atg ctt cac cag ctg ctc tcc ttg cac ggt ggc agc acc        1872
Ile Thr Asp Met Leu His Gln Leu Leu Ser Leu His Gly Gly Ser Thr
610                 615                 620 ccc ggc agc ggc ggc ccc ccc aga gag ggc ggg gcc cac atc acc cag        1920
Pro Gly Ser Gly Gly Pro Pro Arg Glu Gly Gly Ala His Ile Thr Gln
625                 630                 635                 640 ccc tgc ggc agt ggc ggc tcc gtc gac cct gag ctc ttc ctg ccc agc        1968
Pro Cys Gly Ser Gly Gly Ser Val Asp Pro Glu Leu Phe Leu Pro Ser
                645                 650                 655 aac acc ctg ccc acc tac gag cag ctg acc gtg ccc agg agg ggc ccc        2016
Asn Thr Leu Pro Thr Tyr Glu Gln Leu Thr Val Pro Arg Arg Gly Pro
            660                 665                 670 gat gag ggg tcc                                                         2028
Asp Glu Gly Ser
        675

<210> SEQ ID NO 2
<211> LENGTH: 676
<212> TYPE: PRT
<213> ORGANISM: Homo sapiens

<400> SEQUENCE: 2

Met Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
                20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro Pro
        50                  55                  60

Ala Ser Pro Ala Ala Pro Ala Ala Pro Pro Val Ala Ser Asp Leu Gly
65                  70                  75                  80
```

-continued

```
Pro Arg Pro Pro Val Ser Leu Asp Pro Arg Val Ser Ile Tyr Ser Thr
                85                  90                  95
Arg Arg Pro Val Leu Ala Arg Thr His Val Gln Gly Arg Val Tyr Asn
            100                 105                 110
Phe Leu Glu Arg Pro Thr Gly Trp Lys Cys Phe Val Tyr His Phe Ala
        115                 120                 125
Val Phe Leu Ile Val Leu Val Cys Leu Ile Phe Ser Val Leu Ser Thr
    130                 135                 140
Ile Glu Gln Tyr Ala Ala Leu Ala Thr Gly Thr Leu Phe Trp Met Glu
145                 150                 155                 160
Ile Val Leu Val Val Phe Phe Gly Thr Glu Tyr Val Val Arg Leu Trp
                165                 170                 175
Ser Ala Gly Cys Arg Ser Lys Tyr Val Gly Leu Trp Gly Arg Leu Arg
            180                 185                 190
Phe Ala Arg Lys Pro Ile Ser Ile Ile Asp Leu Ile Val Val Val Ala
        195                 200                 205
Ser Met Val Val Leu Cys Val Gly Ser Lys Gly Gln Val Phe Ala Thr
    210                 215                 220
Ser Ala Ile Arg Gly Ile Arg Phe Leu Gln Ile Leu Arg Met Leu His
225                 230                 235                 240
Val Asp Arg Gln Gly Gly Thr Trp Arg Leu Leu Gly Ser Val Val Phe
                245                 250                 255
Ile His Arg Gln Glu Leu Ile Thr Thr Leu Tyr Ile Gly Phe Leu Gly
            260                 265                 270
Leu Ile Phe Ser Ser Tyr Phe Val Tyr Leu Ala Glu Lys Asp Ala Val
        275                 280                 285
Asn Glu Ser Gly Arg Val Glu Phe Gly Ser Tyr Ala Asp Ala Leu Trp
    290                 295                 300
Trp Gly Val Val Thr Val Thr Thr Ile Gly Tyr Gly Asp Lys Val Pro
305                 310                 315                 320
Gln Thr Trp Val Gly Lys Thr Ile Ala Ser Cys Phe Ser Val Phe Ala
                325                 330                 335
Ile Ser Phe Phe Ala Leu Pro Ala Gly Ile Leu Gly Ser Gly Phe Ala
            340                 345                 350
Leu Lys Val Gln Gln Lys Gln Arg Gln Lys His Phe Asn Arg Gln Ile
        355                 360                 365
Pro Ala Ala Ala Ser Leu Ile Gln Thr Ala Trp Arg Cys Tyr Ala Ala
    370                 375                 380
Glu Asn Pro Asp Ser Ser Thr Trp Lys Ile Tyr Ile Arg Lys Ala Pro
385                 390                 395                 400
Arg Ser His Thr Leu Leu Ser Pro Ser Pro Lys Pro Lys Lys Ser Val
                405                 410                 415
Val Val Lys Lys Lys Lys Phe Lys Leu Asp Lys Asp Asn Gly Val Thr
            420                 425                 430
Pro Gly Glu Lys Met Leu Thr Val Pro His Ile Thr Cys Asp Pro Pro
        435                 440                 445
Glu Glu Arg Arg Leu Asp His Phe Ser Val Asp Gly Tyr Asp Ser Ser
    450                 455                 460
Val Arg Lys Ser Pro Thr Leu Leu Glu Val Ser Met Pro His Phe Met
465                 470                 475                 480
Arg Thr Asn Ser Phe Ala Glu Asp Leu Asp Leu Glu Gly Glu Thr Leu
                485                 490                 495
Leu Thr Pro Ile Thr His Ile Ser Gln Leu Arg Glu His His Arg Ala
```

-continued

```
                     500                 505                 510
Thr Ile Lys Val Ile Arg Arg Met Gln Tyr Phe Val Ala Lys Lys Lys
                515                 520                 525

Phe Gln Gln Ala Arg Lys Pro Tyr Asp Val Arg Asp Val Ile Glu Gln
            530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
                595                 600                 605

Ile Thr Asp Met Leu His Gln Leu Leu Ser Leu His Gly Gly Ser Thr
        610                 615                 620

Pro Gly Ser Gly Gly Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
                660                 665                 670

Asp Glu Gly Ser
            675

<210> SEQ ID NO 3
<211> LENGTH: 6048
<212> TYPE: DNA
<213> ORGANISM: Homo sapiens
<220> FEATURE:
<221> NAME/KEY: CDS
<222> LOCATION: (1)..(6048)

<400> SEQUENCE: 3 atg gca aac ttc cta tta cct cgg ggc acc agc agc ttc cgc agg ttc      48
Met Ala Asn Phe Leu Leu Pro Arg Gly Thr Ser Ser Phe Arg Arg Phe
  1               5                  10                  15 aca cgg gag tcc ctg gca gcc atc gag aag cgc atg gcg gag aag caa      96
Thr Arg Glu Ser Leu Ala Ala Ile Glu Lys Arg Met Ala Glu Lys Gln
                 20                  25                  30 gcc cgc ggc tca acc acc ttg cag gag agc cga gag ggg ctg ccc gag     144
Ala Arg Gly Ser Thr Thr Leu Gln Glu Ser Arg Glu Gly Leu Pro Glu
             35                  40                  45 gag gag gct ccc cgg ccc cag ctg gac ctg cag gcc tcc aaa aag ctg     192
Glu Glu Ala Pro Arg Pro Gln Leu Asp Leu Gln Ala Ser Lys Lys Leu
         50                  55                  60 cca gat ctc tat ggc aat cca ccc caa gag ctc atc gga gag ccc ctg     240
Pro Asp Leu Tyr Gly Asn Pro Pro Gln Glu Leu Ile Gly Glu Pro Leu
 65                  70                  75                  80 gag gac ctg gac ccc ttc tat agc acc caa aag act ttc atc gta ctg     288
Glu Asp Leu Asp Pro Phe Tyr Ser Thr Gln Lys Thr Phe Ile Val Leu
                 85                  90                  95 aat aaa ggc aag acc atc ttc cgg ttc agt gcc acc aac gcc ttg tat     336
Asn Lys Gly Lys Thr Ile Phe Arg Phe Ser Ala Thr Asn Ala Leu Tyr
            100                 105                 110 gtc ctc agt ccc ttc cac cca gtt cgg aga gcg gct gtg aag att ctg     384
Val Leu Ser Pro Phe His Pro Val Arg Arg Ala Ala Val Lys Ile Leu
        115                 120                 125 gtt cac tcg ctc ttc aac atg ctc atc atg tgc acc atc ctc acc aac     432
```

```
Val His Ser Leu Phe Asn Met Leu Ile Met Cys Thr Ile Leu Thr Asn
    130                 135                 140 tgc gtg ttc atg gcc cag cac gac cct cca ccc tgg acc aag tat gtc        480
Cys Val Phe Met Ala Gln His Asp Pro Pro Pro Trp Thr Lys Tyr Val
145                 150                 155                 160 gag tac acc ttc acc gcc att tac acc ttt gag tct ctg gtc aag att        528
Glu Tyr Thr Phe Thr Ala Ile Tyr Thr Phe Glu Ser Leu Val Lys Ile
                165                 170                 175 ctg gct cga gct ttc tgc ctg cac gcg ttc act ttc ctt cgg gac cca        576
Leu Ala Arg Ala Phe Cys Leu His Ala Phe Thr Phe Leu Arg Asp Pro
            180                 185                 190 tgg aac tgg ctg gac ttt agt gtg att atc atg gca tac aca act gaa        624
Trp Asn Trp Leu Asp Phe Ser Val Ile Ile Met Ala Tyr Thr Thr Glu
        195                 200                 205 ttt gtg gac ctg ggc aat gtc tca gcc tta cgc acc ttc cga gtc ctc        672
Phe Val Asp Leu Gly Asn Val Ser Ala Leu Arg Thr Phe Arg Val Leu
    210                 215                 220 cgg gcc ctg aaa act ata tca gtc att tca ggg ctg aag acc atc gtg        720
Arg Ala Leu Lys Thr Ile Ser Val Ile Ser Gly Leu Lys Thr Ile Val
225                 230                 235                 240 ggg gcc ctg atc cag tct gtg aag aag ctg gct gat gtg atg gtc ctc        768
Gly Ala Leu Ile Gln Ser Val Lys Lys Leu Ala Asp Val Met Val Leu
                245                 250                 255 aca gtc ttc tgc ctc agc gtc ttt gcc ctc atc ggc ctg cag ctc ttc        816
Thr Val Phe Cys Leu Ser Val Phe Ala Leu Ile Gly Leu Gln Leu Phe
            260                 265                 270 atg ggc aac cta agg cac aag tgt gtg cgc aac ttc aca gcg ctc aac        864
Met Gly Asn Leu Arg His Lys Cys Val Arg Asn Phe Thr Ala Leu Asn
        275                 280                 285 ggc acc aac ggc tcc gtg gag gcc gac ggc ttg gtc tgg gaa tcc ctg        912
Gly Thr Asn Gly Ser Val Glu Ala Asp Gly Leu Val Trp Glu Ser Leu
    290                 295                 300 gac ctt tac ctc agt gat cca gaa aat tac ctg ctc aag aac ggc acc        960
Asp Leu Tyr Leu Ser Asp Pro Glu Asn Tyr Leu Leu Lys Asn Gly Thr
305                 310                 315                 320 tct gat gtg tta ctg tgt ggg aac agc tct gac gct ggg aca tgt ccg       1008
Ser Asp Val Leu Leu Cys Gly Asn Ser Ser Asp Ala Gly Thr Cys Pro
                325                 330                 335 gag ggc tac cgg tgc cta aag gca ggc gag aac ccc gac cac ggc tac       1056
Glu Gly Tyr Arg Cys Leu Lys Ala Gly Glu Asn Pro Asp His Gly Tyr
            340                 345                 350 acc agc ttc gat tcc ttt gcc tgg gcc ttt ctt gca ctc ttc cgc ctg       1104
Thr Ser Phe Asp Ser Phe Ala Trp Ala Phe Leu Ala Leu Phe Arg Leu
        355                 360                 365 atg acg cag gac tgc tgg gag cgc ctc tat cag cag acc ctc agg tcc       1152
Met Thr Gln Asp Cys Trp Glu Arg Leu Tyr Gln Gln Thr Leu Arg Ser
    370                 375                 380 gca ggg aag atc tac atg atc ttc ttc atg ctt gtc atc ttc ctg ggg       1200
Ala Gly Lys Ile Tyr Met Ile Phe Phe Met Leu Val Ile Phe Leu Gly
385                 390                 395                 400 tcc ttc tac ctg gtg aac ctg atc ctg gcc gtg gtc gca atg gcc tat       1248
Ser Phe Tyr Leu Val Asn Leu Ile Leu Ala Val Val Ala Met Ala Tyr
                405                 410                 415 gag gag caa aac caa gcc acc atc gct gag acc gag gag aag gaa aag       1296
Glu Glu Gln Asn Gln Ala Thr Ile Ala Glu Thr Glu Glu Lys Glu Lys
            420                 425                 430 cgc ttc cag gag gcc atg gaa atg ctc aag aaa gaa cac gag gcc ctc       1344
Arg Phe Gln Glu Ala Met Glu Met Leu Lys Lys Glu His Glu Ala Leu
        435                 440                 445
```

```
acc atc agg ggt gtg gat acc gtg tcc cgt agc tcc ttg gag atg tcc    1392
Thr Ile Arg Gly Val Asp Thr Val Ser Arg Ser Ser Leu Glu Met Ser
    450                 455                 460 cct ttg gcc cca gta aac agc cat gag aga aga agc aag agg aga aaa    1440
Pro Leu Ala Pro Val Asn Ser His Glu Arg Arg Ser Lys Arg Arg Lys
465                 470                 475                 480 cgg atg tct tca gga act gag gag tgt ggg gag gac agg ctc ccc aag    1488
Arg Met Ser Ser Gly Thr Glu Glu Cys Gly Glu Asp Arg Leu Pro Lys
                485                 490                 495 tct gac tca gaa gat ggt ccc aga gca atg aat cat ctc agc ctc acc    1536
Ser Asp Ser Glu Asp Gly Pro Arg Ala Met Asn His Leu Ser Leu Thr
        500                 505                 510 cgt ggc ctc agc agg act tct atg aag cca cgt tcc agc cgc ggg agc    1584
Arg Gly Leu Ser Arg Thr Ser Met Lys Pro Arg Ser Ser Arg Gly Ser
            515                 520                 525 att ttc acc ttt cgc agg cga gac ctg ggt tct gaa gca gat ttt gca    1632
Ile Phe Thr Phe Arg Arg Arg Asp Leu Gly Ser Glu Ala Asp Phe Ala
    530                 535                 540 gat gat gaa aac agc aca gcg cgg gag agc gag agc cac cac aca tca    1680
Asp Asp Glu Asn Ser Thr Ala Arg Glu Ser Glu Ser His His Thr Ser
545                 550                 555                 560 ctg ctg gtg ccc tgg ccc ctg cgc cgg acc agt gcc cag gga cag ccc    1728
Leu Leu Val Pro Trp Pro Leu Arg Arg Thr Ser Ala Gln Gly Gln Pro
                565                 570                 575 agt ccc gga acc tcg gct cct ggc cac gcc ctc cat ggc aaa aag aac    1776
Ser Pro Gly Thr Ser Ala Pro Gly His Ala Leu His Gly Lys Lys Asn
        580                 585                 590 agc act gtg gac tgc aat ggg gtg gtc tca tta ctg ggg gca ggc gac    1824
Ser Thr Val Asp Cys Asn Gly Val Val Ser Leu Leu Gly Ala Gly Asp
            595                 600                 605 cca gag gcc aca tcc cca gga agc cac ctc ctc cgc cct gtg atg cta    1872
Pro Glu Ala Thr Ser Pro Gly Ser His Leu Leu Arg Pro Val Met Leu
    610                 615                 620 gag cac ccg cca gac acg acc acg cca tcg gag gag cca ggc ggc ccc    1920
Glu His Pro Pro Asp Thr Thr Thr Pro Ser Glu Glu Pro Gly Gly Pro
625                 630                 635                 640 cag atg ctg acc tcc cag gct ccg tgt gta gat ggc ttc gag gag cca    1968
Gln Met Leu Thr Ser Gln Ala Pro Cys Val Asp Gly Phe Glu Glu Pro
                645                 650                 655 gga gca cgg cag cgg gcc ctc agc gca gtc agc gtc ctc aca agc gca    2016
Gly Ala Arg Gln Arg Ala Leu Ser Ala Val Ser Val Leu Thr Ser Ala
        660                 665                 670 ctg gaa gag tta gag gag tct cgc cac aag tgt cca cca tgc tgg aac    2064
Leu Glu Glu Leu Glu Glu Ser Arg His Lys Cys Pro Pro Cys Trp Asn
            675                 680                 685 cgt ctc gcc cag cgc tac ctg atc tgg gag tgc tgc ccg ctg tgg atg    2112
Arg Leu Ala Gln Arg Tyr Leu Ile Trp Glu Cys Cys Pro Leu Trp Met
    690                 695                 700 tcc atc aag cag gga gtg aag ttg gtg gtc atg gac ccg ttt act gac    2160
Ser Ile Lys Gln Gly Val Lys Leu Val Val Met Asp Pro Phe Thr Asp
705                 710                 715                 720 ctc acc atc act atg tgc atc gta ctc aac aca ctc ttc atg gcg ctg    2208
Leu Thr Ile Thr Met Cys Ile Val Leu Asn Thr Leu Phe Met Ala Leu
                725                 730                 735 gag cac tac aac atg aca agt gaa ttc gag gag atg ctg cag gtc gga    2256
Glu His Tyr Asn Met Thr Ser Glu Phe Glu Glu Met Leu Gln Val Gly
        740                 745                 750 aac ctg gtc ttc aca ggg att ttc aca gca gag atg acc ttc aag atc    2304
Asn Leu Val Phe Thr Gly Ile Phe Thr Ala Glu Met Thr Phe Lys Ile
            755                 760                 765
```

```
att gcc ctc gac ccc tac tac tac ttc caa cag ggc tgg aac atc ttc      2352
Ile Ala Leu Asp Pro Tyr Tyr Tyr Phe Gln Gln Gly Trp Asn Ile Phe
    770             775                 780 gac agc atc atc gtc atc ctt agc ctc atg gag ctg ggc ctg tcc cgc      2400
Asp Ser Ile Ile Val Ile Leu Ser Leu Met Glu Leu Gly Leu Ser Arg
785             790                 795                 800 atg agc aac ttg tcg gtg ctg cgc tcc ttc cgc ctg ctg cgg gtc ttc      2448
Met Ser Asn Leu Ser Val Leu Arg Ser Phe Arg Leu Leu Arg Val Phe
                805                 810                 815 aag ctg gcc aaa tca tgg ccc acc ctg aac aca ctc atc aag atc atc      2496
Lys Leu Ala Lys Ser Trp Pro Thr Leu Asn Thr Leu Ile Lys Ile Ile
            820                 825                 830 ggg aac tca gtg ggg gca ctg ggg aac ctg aca ctg gtg cta gcc atc      2544
Gly Asn Ser Val Gly Ala Leu Gly Asn Leu Thr Leu Val Leu Ala Ile
        835                 840                 845 atc gtg ttc atc ttt gct gtg gtg ggc atg cag ctc ttt ggc aag aac      2592
Ile Val Phe Ile Phe Ala Val Val Gly Met Gln Leu Phe Gly Lys Asn
850                 855                 860 tac tcg gag ctg agg gac agc gac tca ggc ctg ctg cct cgc tgg cac      2640
Tyr Ser Glu Leu Arg Asp Ser Asp Ser Gly Leu Leu Pro Arg Trp His
865             870                 875                 880 atg atg gac ttc ttt cat gcc ttc cta atc atc ttc cgc atc ctc tgt      2688
Met Met Asp Phe Phe His Ala Phe Leu Ile Ile Phe Arg Ile Leu Cys
                885                 890                 895 gga gag tgg atc gag acc atg tgg gac tgc atg gag gtg tcg ggg cag      2736
Gly Glu Trp Ile Glu Thr Met Trp Asp Cys Met Glu Val Ser Gly Gln
            900                 905                 910 tca tta tgc ctg ctg gtc ttc ttg ctt gtt atg gtc att ggc aac ctt      2784
Ser Leu Cys Leu Leu Val Phe Leu Leu Val Met Val Ile Gly Asn Leu
        915                 920                 925 gtg gtc ctg aat ctc ttc ctg gcc ttg ctg ctc agc tcc ttc agt gca      2832
Val Val Leu Asn Leu Phe Leu Ala Leu Leu Leu Ser Ser Phe Ser Ala
    930                 935                 940 gac aac ctc aca gcc cct gat gag gac aga gag atg aac aac ctc cag      2880
Asp Asn Leu Thr Ala Pro Asp Glu Asp Arg Glu Met Asn Asn Leu Gln
945                 950                 955                 960 ctg gcc ctg gcc cgc atc cag agg ggc ctg cgc ttt gtc aag cgg acc      2928
Leu Ala Leu Ala Arg Ile Gln Arg Gly Leu Arg Phe Val Lys Arg Thr
                965                 970                 975 acc tgg gat ttc tgc tgt ggt ctc ctg cgg cac cgg cct cag aag ccc      2976
Thr Trp Asp Phe Cys Cys Gly Leu Leu Arg His Arg Pro Gln Lys Pro
            980                 985                 990 gca gcc ctt gcc gcc cag ggc cag ctg ccc agc tgc att gcc acc ccc      3024
Ala Ala Leu Ala Ala Gln Gly Gln Leu Pro Ser Cys Ile Ala Thr Pro
        995                 1000                1005 tac tcc ccg cca ccc cca gag acg gag aag gtg cct ccc acc cgc aag      3072
Tyr Ser Pro Pro Pro Pro Glu Thr Glu Lys Val Pro Pro Thr Arg Lys
    1010                1015                1020 gaa aca cag ttt gag gaa ggc gag caa cca ggc cag ggc acc ccc ggg      3120
Glu Thr Gln Phe Glu Glu Gly Glu Gln Pro Gly Gln Gly Thr Pro Gly
1025                1030                1035                1040 gat cca gag ccc gtg tgt gtg ccc atc gct gtg gcc gag tca gac aca      3168
Asp Pro Glu Pro Val Cys Val Pro Ile Ala Val Ala Glu Ser Asp Thr
                1045                1050                1055 gat gac caa gaa gag gat gag gag aac agc ctg ggc acg gag gag gag      3216
Asp Asp Gln Glu Glu Asp Glu Glu Asn Ser Leu Gly Thr Glu Glu Glu
            1060                1065                1070 tcc agc aag cag cag gaa tcc cag cct gtg tcc ggc tgg ccc aga ggc      3264
Ser Ser Lys Gln Gln Glu Ser Gln Pro Val Ser Gly Trp Pro Arg Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 1075 |   |     |     |     | 1080 |   |     |     |     | 1085 |   |     |     |      |
| cct | ccg | gat | tcc | agg | acc | tgg | agc | cag | gtg | tca | gcg | act | gcc | tcc | tct | 3312 |
| Pro | Pro | Asp | Ser | Arg | Thr | Trp | Ser | Gln | Val | Ser | Ala | Thr | Ala | Ser | Ser |      |
|     |     | 1090 |   |     |     |     | 1095 |   |     |     |     | 1100 |   |     |     |      |
| gag | gcc | gag | gcc | agt | gca | tct | cag | gcc | gac | tgg | cgg | cag | cag | tgg | aaa | 3360 |
| Glu | Ala | Glu | Ala | Ser | Ala | Ser | Gln | Ala | Asp | Trp | Arg | Gln | Gln | Trp | Lys |      |
| 1105 |     |     |     | 1110 |   |     |     |     | 1115 |   |     |     |     | 1120 |   |      |
| gcg | gaa | ccc | cag | gcc | cca | ggg | tgc | ggt | gag | acc | cca | gag | gac | agt | tgc | 3408 |
| Ala | Glu | Pro | Gln | Ala | Pro | Gly | Cys | Gly | Glu | Thr | Pro | Glu | Asp | Ser | Cys |      |
|     |     |     |     | 1125 |   |     |     |     | 1130 |   |     |     |     | 1135 |   |      |
| tcc | gag | ggc | agc | aca | gca | gac | atg | acc | aac | acc | gct | gag | ctc | ctg | gag | 3456 |
| Ser | Glu | Gly | Ser | Thr | Ala | Asp | Met | Thr | Asn | Thr | Ala | Glu | Leu | Leu | Glu |      |
|     |     |     | 1140 |   |     |     |     | 1145 |   |     |     |     | 1150 |   |     |      |
| cag | atc | cct | gac | ctc | ggc | cag | gat | gtc | aag | gac | cca | gag | gac | tgc | ttc | 3504 |
| Gln | Ile | Pro | Asp | Leu | Gly | Gln | Asp | Val | Lys | Asp | Pro | Glu | Asp | Cys | Phe |      |
|     |     | 1155 |   |     |     |     | 1160 |   |     |     |     | 1165 |   |     |     |      |
| act | gaa | ggc | tgt | gtc | cgg | cgc | tgt | ccc | tgc | tgt | gcg | gtg | gac | acc | aca | 3552 |
| Thr | Glu | Gly | Cys | Val | Arg | Arg | Cys | Pro | Cys | Cys | Ala | Val | Asp | Thr | Thr |      |
|     |     | 1170 |   |     |     |     | 1175 |   |     |     |     | 1180 |   |     |     |      |
| cag | gcc | cca | ggg | aag | gtc | tgg | tgg | cgg | ttg | cgc | aag | acc | tgc | tac | cac | 3600 |
| Gln | Ala | Pro | Gly | Lys | Val | Trp | Trp | Arg | Leu | Arg | Lys | Thr | Cys | Tyr | His |      |
| 1185 |   |     |     | 1190 |   |     |     |     | 1195 |   |     |     |     | 1200 |   |      |
| atc | gtg | gag | cac | agc | tgg | ttc | gag | aca | ttc | atc | atc | ttc | atg | atc | cta | 3648 |
| Ile | Val | Glu | His | Ser | Trp | Phe | Glu | Thr | Phe | Ile | Ile | Phe | Met | Ile | Leu |      |
|     |     |     |     | 1205 |   |     |     |     | 1210 |   |     |     |     | 1215 |   |      |
| ctc | agc | agt | gga | gcg | ctg | gcc | ttc | gag | gac | atc | tac | cta | gag | gag | cgg | 3696 |
| Leu | Ser | Ser | Gly | Ala | Leu | Ala | Phe | Glu | Asp | Ile | Tyr | Leu | Glu | Glu | Arg |      |
|     |     |     | 1220 |   |     |     |     | 1225 |   |     |     |     | 1230 |   |     |      |
| aag | acc | atc | aag | gtt | ctg | ctt | gag | tat | gcc | gac | aag | atg | ttc | aca | tat | 3744 |
| Lys | Thr | Ile | Lys | Val | Leu | Leu | Glu | Tyr | Ala | Asp | Lys | Met | Phe | Thr | Tyr |      |
|     |     | 1235 |   |     |     |     | 1240 |   |     |     |     | 1245 |   |     |     |      |
| gtc | ttc | gtg | ctg | gag | atg | ctg | ctc | aag | tgg | gtg | gcc | tac | ggc | ttc | aag | 3792 |
| Val | Phe | Val | Leu | Glu | Met | Leu | Leu | Lys | Trp | Val | Ala | Tyr | Gly | Phe | Lys |      |
|     |     | 1250 |   |     |     |     | 1255 |   |     |     |     | 1260 |   |     |     |      |
| aag | tac | ttc | acc | aat | gcc | tgg | tgc | tgg | ctc | gac | ttc | ctc | atc | gta | gac | 3840 |
| Lys | Tyr | Phe | Thr | Asn | Ala | Trp | Cys | Trp | Leu | Asp | Phe | Leu | Ile | Val | Asp |      |
| 1265 |   |     |     | 1270 |   |     |     |     | 1275 |   |     |     |     | 1280 |   |      |
| gtc | tct | ctg | gtc | agc | ctg | gtg | gcc | aac | acc | ctg | ggc | ttt | gcc | gag | atg | 3888 |
| Val | Ser | Leu | Val | Ser | Leu | Val | Ala | Asn | Thr | Leu | Gly | Phe | Ala | Glu | Met |      |
|     |     |     |     | 1285 |   |     |     |     | 1290 |   |     |     |     | 1295 |   |      |
| ggc | ccc | atc | aag | tca | ctg | cgg | acg | ctg | cgt | gca | ctc | cgt | cct | ctg | aga | 3936 |
| Gly | Pro | Ile | Lys | Ser | Leu | Arg | Thr | Leu | Arg | Ala | Leu | Arg | Pro | Leu | Arg |      |
|     |     |     | 1300 |   |     |     |     | 1305 |   |     |     |     | 1310 |   |     |      |
| gct | ctg | tca | cga | ttt | gag | ggc | atg | agg | gtg | gtg | gtc | aat | gcc | ctg | gtg | 3984 |
| Ala | Leu | Ser | Arg | Phe | Glu | Gly | Met | Arg | Val | Val | Val | Asn | Ala | Leu | Val |      |
|     |     |     | 1315 |   |     |     |     | 1320 |   |     |     |     | 1325 |   |     |      |
| ggc | gcc | atc | ccg | tcc | atc | atg | aac | gtc | ctc | ctc | gtc | tgc | ctc | atc | ttc | 4032 |
| Gly | Ala | Ile | Pro | Ser | Ile | Met | Asn | Val | Leu | Leu | Val | Cys | Leu | Ile | Phe |      |
|     |     | 1330 |   |     |     |     | 1335 |   |     |     |     | 1340 |   |     |     |      |
| tgg | ctc | atc | ttc | agc | atc | atg | ggc | gtg | aac | ctc | ttt | gcg | ggg | aag | ttt | 4080 |
| Trp | Leu | Ile | Phe | Ser | Ile | Met | Gly | Val | Asn | Leu | Phe | Ala | Gly | Lys | Phe |      |
| 1345 |   |     |     | 1350 |   |     |     |     | 1355 |   |     |     |     | 1360 |   |      |
| ggg | agg | tgc | atc | aac | cag | aca | gag | gga | gac | ttg | cct | ttg | aac | tac | acc | 4128 |
| Gly | Arg | Cys | Ile | Asn | Gln | Thr | Glu | Gly | Asp | Leu | Pro | Leu | Asn | Tyr | Thr |      |
|     |     |     |     | 1365 |   |     |     |     | 1370 |   |     |     |     | 1375 |   |      |
| atc | gtg | aac | aac | aag | agc | cag | tgt | gag | tcc | ttg | aac | ttg | acc | gga | gaa | 4176 |
| Ile | Val | Asn | Asn | Lys | Ser | Gln | Cys | Glu | Ser | Leu | Asn | Leu | Thr | Gly | Glu |      |
|     |     |     | 1380 |   |     |     |     | 1385 |   |     |     |     | 1390 |   |     |      |
| ttg | tac | tgg | acc | aag | gtg | aaa | gtc | aac | ttt | gac | aac | gtg | ggg | gcc | ggg | 4224 |

-continued

```
                Leu Tyr Trp Thr Lys Val Lys Val Asn Phe Asp Asn Val Gly Ala Gly
                        1395                1400                1405 tac ctg gcc ctt ctg cag gtg gca aca ttt aaa ggc tgg atg gac att          4272
Tyr Leu Ala Leu Leu Gln Val Ala Thr Phe Lys Gly Trp Met Asp Ile
    1410                1415                1420 atg tat gca gct gtg gac tcc agg ggg tat gaa gag cag cct cag tgg         4320
Met Tyr Ala Ala Val Asp Ser Arg Gly Tyr Glu Glu Gln Pro Gln Trp
1425                1430                1435                1440 gaa tac aac ctc tac atg tac atc tat ttt gtc att ttc atc atc ttt         4368
Glu Tyr Asn Leu Tyr Met Tyr Ile Tyr Phe Val Ile Phe Ile Ile Phe
                1445                1450                1455 ggg tct ttc ttc acc ctg aac ctc ttt att ggt gtc atc att gac aac         4416
Gly Ser Phe Phe Thr Leu Asn Leu Phe Ile Gly Val Ile Ile Asp Asn
            1460                1465                1470 ttc aac caa cag aag aaa aag tta ggg ggc cag gac atc ttc atg aca         4464
Phe Asn Gln Gln Lys Lys Lys Leu Gly Gly Gln Asp Ile Phe Met Thr
        1475                1480                1485 gag gag cag aag aag tac tac aat gcc atg aag aag ctg ggc tcc aag         4512
Glu Glu Gln Lys Lys Tyr Tyr Asn Ala Met Lys Lys Leu Gly Ser Lys
    1490                1495                1500 aag ccc cag aag ccc atc cca cgg ccc ctg aac aag tac cag ggc ttc         4560
Lys Pro Gln Lys Pro Ile Pro Arg Pro Leu Asn Lys Tyr Gln Gly Phe
1505                1510                1515                1520 ata ttc gac att gtg acc aag cag gcc ttt gac gtc acc atc atg ttt         4608
Ile Phe Asp Ile Val Thr Lys Gln Ala Phe Asp Val Thr Ile Met Phe
                1525                1530                1535 ctg atc tgc ttg aat atg gtg acc atg atg gtg gag aca gat gac caa         4656
Leu Ile Cys Leu Asn Met Val Thr Met Met Val Glu Thr Asp Asp Gln
            1540                1545                1550 agt cct gag aaa atc aac atc ttg gcc aag atc aac ctg ctc ttt gtg         4704
Ser Pro Glu Lys Ile Asn Ile Leu Ala Lys Ile Asn Leu Leu Phe Val
        1555                1560                1565 gcc atc ttc aca ggc gag tgt att gtc aag ctg gct gcc ctg cgc cac         4752
Ala Ile Phe Thr Gly Glu Cys Ile Val Lys Leu Ala Ala Leu Arg His
    1570                1575                1580 tac tac ttc acc aac agc tgg aat atc ttc gac ttc gtg gtt gtc atc         4800
Tyr Tyr Phe Thr Asn Ser Trp Asn Ile Phe Asp Phe Val Val Val Ile
1585                1590                1595                1600 ctc tcc atc gtg ggc act gtg ctc tcg gac atc atc cag aag tac ttc         4848
Leu Ser Ile Val Gly Thr Val Leu Ser Asp Ile Ile Gln Lys Tyr Phe
                1605                1610                1615 ttc tcc ccg acg ctc ttc cga gtc atc cgc ctg gcc cga ata ggc cgc         4896
Phe Ser Pro Thr Leu Phe Arg Val Ile Arg Leu Ala Arg Ile Gly Arg
            1620                1625                1630 atc ctc aga ctg atc cga ggg gcc aag ggg atc cgc acg ctg ctc ttt         4944
Ile Leu Arg Leu Ile Arg Gly Ala Lys Gly Ile Arg Thr Leu Leu Phe
        1635                1640                1645 gcc ctc atg atg tcc ctg cct gcc ctc ttc aac atc ggg ctg ctg ctc         4992
Ala Leu Met Met Ser Leu Pro Ala Leu Phe Asn Ile Gly Leu Leu Leu
    1650                1655                1660 ttc ctc gtc atg ttc atc tac tcc atc ttt ggc atg gcc aac ttc gct         5040
Phe Leu Val Met Phe Ile Tyr Ser Ile Phe Gly Met Ala Asn Phe Ala
1665                1670                1675                1680 tat gtc aag tgg gag gct ggc atc gac gac atg ttc aac ttc cag acc         5088
Tyr Val Lys Trp Glu Ala Gly Ile Asp Asp Met Phe Asn Phe Gln Thr
                1685                1690                1695 ttc gcc aac agc atg ctg tgc ctc ttc cag atc acc acg tcg gcc ggc         5136
Phe Ala Asn Ser Met Leu Cys Leu Phe Gln Ile Thr Thr Ser Ala Gly
            1700                1705                1710
```

```
tgg gat ggc ctc ctc agc ccc atc ctc aac act ggg ccg ccc tac tgc    5184
Trp Asp Gly Leu Leu Ser Pro Ile Leu Asn Thr Gly Pro Pro Tyr Cys
1715                1720                1725 gac ccc act ctg ccc aac agc aat ggc tct cgg ggg gac tgc ggg agc    5232
Asp Pro Thr Leu Pro Asn Ser Asn Gly Ser Arg Gly Asp Cys Gly Ser
        1730                1735                1740 cca gcc gtg ggc atc ctc ttc ttc acc acc tac atc atc tcc ttc        5280
Pro Ala Val Gly Ile Leu Phe Phe Thr Thr Tyr Ile Ile Ser Phe
1745                1750                1755                1760 ctc atc gtg gtc aac atg tac att gcc atc atc ctg gag aac ttc agc    5328
Leu Ile Val Val Asn Met Tyr Ile Ala Ile Ile Leu Glu Asn Phe Ser
                1765                1770                1775 gtg gcc acg gag gag agc acc gag ccc ctg agt gag gac gac ttc gat    5376
Val Ala Thr Glu Glu Ser Thr Glu Pro Leu Ser Glu Asp Asp Phe Asp
        1780                1785                1790 atg ttc tat gag atc tgg gag aaa ttt gac cca gag gcc act cag ttt    5424
Met Phe Tyr Glu Ile Trp Glu Lys Phe Asp Pro Glu Ala Thr Gln Phe
            1795                1800                1805 att gag tat tcg gtc ctg tct gac ttt gcc gac gcc ctg tct gag cca    5472
Ile Glu Tyr Ser Val Leu Ser Asp Phe Ala Asp Ala Leu Ser Glu Pro
1810                1815                1820 ctc cgt atc gcc aag ccc aac cag ata agc ctc atc aac atg gac ctg    5520
Leu Arg Ile Ala Lys Pro Asn Gln Ile Ser Leu Ile Asn Met Asp Leu
1825                1830                1835                1840 ccc atg gtg agt ggg gac cgc atc cat tgc atg gac att ctc ttt gcc    5568
Pro Met Val Ser Gly Asp Arg Ile His Cys Met Asp Ile Leu Phe Ala
            1845                1850                1855 ttc acc aaa agg gtc ctg ggg gag tct ggg gag atg gac gcc ctg aag    5616
Phe Thr Lys Arg Val Leu Gly Glu Ser Gly Glu Met Asp Ala Leu Lys
        1860                1865                1870 atc cag atg gag gag aag ttc atg gca gcc aac cca tcc aag atc tcc    5664
Ile Gln Met Glu Glu Lys Phe Met Ala Ala Asn Pro Ser Lys Ile Ser
    1875                1880                1885 tac gag ccc atc acc acc aca ctc cgg cgc aag cac gaa gag gtg tcg    5712
Tyr Glu Pro Ile Thr Thr Thr Leu Arg Arg Lys His Glu Glu Val Ser
        1890                1895                1900 gcc atg gtt atc cag aga gcc ttc cgc agg cac ctg ctg caa cgc tct    5760
Ala Met Val Ile Gln Arg Ala Phe Arg Arg His Leu Leu Gln Arg Ser
1905                1910                1915                1920 ttg aag cat gcc tcc ttc ctc ttc cgt cag cag gcg ggc agc ggc ctc    5808
Leu Lys His Ala Ser Phe Leu Phe Arg Gln Gln Ala Gly Ser Gly Leu
            1925                1930                1935 tcc gaa gag gat gcc cct gag cga gag ggc ctc atc gcc tac gtg atg    5856
Ser Glu Glu Asp Ala Pro Glu Arg Glu Gly Leu Ile Ala Tyr Val Met
        1940                1945                1950 agt gag aac ttc tcc cga ccc ctt ggc cca ccc tcc agc tcc tcc atc    5904
Ser Glu Asn Phe Ser Arg Pro Leu Gly Pro Pro Ser Ser Ser Ser Ile
    1955                1960                1965 tcc tcc act tcc ttc cca ccc tcc tat gac agt gtc act aga gcc acc    5952
Ser Ser Thr Ser Phe Pro Pro Ser Tyr Asp Ser Val Thr Arg Ala Thr
1970                1975                1980 agc gat aac ctc cag gtg cgg ggg tct gac tac agc cac agt gaa gat    6000
Ser Asp Asn Leu Gln Val Arg Gly Ser Asp Tyr Ser His Ser Glu Asp
1985                1990                1995                2000 ctc gcc gac ttc ccc cct tct ccg gac agg gac cgt gag tcc atc gtg    6048
Leu Ala Asp Phe Pro Pro Ser Pro Asp Arg Asp Arg Glu Ser Ile Val
            2005                2010                2015

<210> SEQ ID NO 4
<211> LENGTH: 2016
```

-continued

```
<212> TYPE: PRT
<213> ORGANISM: Homo sapiens

<400> SEQUENCE: 4

Met Ala Asn Phe Leu Leu Pro Arg Gly Thr Ser Ser Phe Arg Arg Phe
  1               5                  10                  15

Thr Arg Glu Ser Leu Ala Ala Ile Glu Lys Arg Met Ala Glu Lys Gln
             20                  25                  30

Ala Arg Gly Ser Thr Thr Leu Gln Glu Ser Arg Glu Gly Leu Pro Glu
         35                  40                  45

Glu Glu Ala Pro Arg Pro Gln Leu Asp Leu Gln Ala Ser Lys Lys Leu
     50                  55                  60

Pro Asp Leu Tyr Gly Asn Pro Pro Gln Glu Leu Ile Gly Glu Pro Leu
 65                  70                  75                  80

Glu Asp Leu Asp Pro Phe Tyr Ser Thr Gln Lys Thr Phe Ile Val Leu
                 85                  90                  95

Asn Lys Gly Lys Thr Ile Phe Arg Phe Ser Ala Thr Asn Ala Leu Tyr
            100                 105                 110

Val Leu Ser Pro Phe His Pro Val Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Ala Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Met Leu Val Ile Phe Leu Gly
385                 390                 395                 400
```

```
Ser Phe Tyr Leu Val Asn Leu Ile Leu Ala Val Val Ala Met Ala Tyr
                405                 410                 415
Glu Glu Gln Asn Gln Ala Thr Ile Ala Glu Thr Glu Lys Glu Lys
        420                 425                 430
Arg Phe Gln Glu Ala Met Glu Met Leu Lys Lys Glu His Glu Ala Leu
        435                 440                 445
Thr Ile Arg Gly Val Asp Thr Val Ser Arg Ser Ser Leu Glu Met Ser
    450                 455                 460
Pro Leu Ala Pro Val Asn Ser His Glu Arg Arg Ser Lys Arg Arg Lys
465                 470                 475                 480
Arg Met Ser Ser Gly Thr Glu Glu Cys Gly Glu Asp Arg Leu Pro Lys
                485                 490                 495
Ser Asp Ser Glu Asp Gly Pro Arg Ala Met Asn His Leu Ser Leu Thr
                500                 505                 510
Arg Gly Leu Ser Arg Thr Ser Met Lys Pro Arg Ser Ser Arg Gly Ser
            515                 520                 525
Ile Phe Thr Phe Arg Arg Arg Asp Leu Gly Ser Glu Ala Asp Phe Ala
            530                 535                 540
Asp Asp Glu Asn Ser Thr Ala Arg Glu Ser Glu Ser His His Thr Ser
545                 550                 555                 560
Leu Leu Val Pro Trp Pro Leu Arg Arg Thr Ser Ala Gln Gly Gln Pro
                565                 570                 575
Ser Pro Gly Thr Ser Ala Pro Gly His Ala Leu His Gly Lys Lys Asn
                580                 585                 590
Ser Thr Val Asp Cys Asn Gly Val Val Ser Leu Leu Gly Ala Gly Asp
            595                 600                 605
Pro Glu Ala Thr Ser Pro Gly Ser His Leu Leu Arg Pro Val Met Leu
            610                 615                 620
Glu His Pro Pro Asp Thr Thr Pro Ser Glu Pro Gly Gly Pro
625                 630                 635                 640
Gln Met Leu Thr Ser Gln Ala Pro Cys Val Asp Gly Phe Glu Glu Pro
                645                 650                 655
Gly Ala Arg Gln Arg Ala Leu Ser Ala Val Ser Val Leu Thr Ser Ala
            660                 665                 670
Leu Glu Glu Leu Glu Glu Ser Arg His Lys Cys Pro Pro Cys Trp Asn
            675                 680                 685
Arg Leu Ala Gln Arg Tyr Leu Ile Trp Glu Cys Cys Pro Leu Trp Met
            690                 695                 700
Ser Ile Lys Gln Gly Val Lys Leu Val Val Met Asp Pro Phe Thr Asp
705                 710                 715                 720
Leu Thr Ile Thr Met Cys Ile Val Leu Asn Thr Leu Phe Met Ala Leu
            725                 730                 735
Glu His Tyr Asn Met Thr Ser Glu Phe Glu Glu Met Leu Gln Val Gly
            740                 745                 750
Asn Leu Val Phe Thr Gly Ile Phe Thr Ala Glu Met Thr Phe Lys Ile
            755                 760                 765
Ile Ala Leu Asp Pro Tyr Tyr Tyr Phe Gln Gln Gly Trp Asn Ile Phe
            770                 775                 780
Asp Ser Ile Ile Val Ile Leu Ser Leu Met Glu Leu Gly Leu Ser Arg
785                 790                 795                 800
Met Ser Asn Leu Ser Val Leu Arg Ser Phe Arg Leu Leu Arg Val Phe
                805                 810                 815
```

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg His Arg Pro Gln Lys Pro
            980                 985                 990

Ala Ala Leu Ala Ala Gln Gly Gln Leu Pro Ser Cys Ile Ala Thr Pro
            995                 1000                1005

Tyr Ser Pro Pro Pro Pro Glu Thr Glu Lys Val Pro Pro Thr Arg Lys
            1010                1015                1020

Glu Thr Gln Phe Glu Glu Gly Glu Gln Pro Gly Gln Gly Thr Pro Gly
1025                1030                1035                1040

Asp Pro Glu Pro Val Cys Val Pro Ile Ala Val Ala Glu Ser Asp Thr
            1045                1050                1055

Asp Asp Gln Glu Glu Asp Glu Glu Asn Ser Leu Gly Thr Glu Glu Glu
            1060                1065                1070

Ser Ser Lys Gln Gln Glu Ser Gln Pro Val Ser Gly Trp Pro Arg Gly
            1075                1080                1085

Pro Pro Asp Ser Arg Thr Trp Ser Gln Val Ser Ala Thr Ala Ser Ser
            1090                1095                1100

Glu Ala Glu Ala Ser Ala Ser Gln Ala Asp Trp Arg Gln Gln Trp Lys
1105                1110                1115                1120

Ala Glu Pro Gln Ala Pro Gly Cys Gly Glu Thr Pro Glu Asp Ser Cys
            1125                1130                1135

Ser Glu Gly Ser Thr Ala Asp Met Thr Asn Thr Ala Glu Leu Leu Glu
            1140                1145                1150

Gln Ile Pro Asp Leu Gly Gln Asp Val Lys Asp Pro Glu Asp Cys Phe
            1155                1160                1165

Thr Glu Gly Cys Val Arg Arg Cys Pro Cys Cys Ala Val Asp Thr Thr
            1170                1175                1180

Gln Ala Pro Gly Lys Val Trp Trp Arg Leu Arg Lys Thr Cys Tyr His
1185                1190                1195                1200

Ile Val Glu His Ser Trp Phe Glu Thr Phe Ile Ile Phe Met Ile Leu
            1205                1210                1215

Leu Ser Ser Gly Ala Leu Ala Phe Glu Asp Ile Tyr Leu Glu Glu Arg
            1220                1225                1230

Lys Thr Ile Lys Val Leu Leu Glu Tyr Ala Asp Lys Met Phe Thr Tyr

-continued

```
            1235                1240                1245
Val Phe Val Leu Glu Met Leu Leu Lys Trp Val Ala Tyr Gly Phe Lys
            1250                1255                1260

Lys Tyr Phe Thr Asn Ala Trp Cys Trp Leu Asp Phe Leu Ile Val Asp
1265                1270                1275                1280

Val Ser Leu Val Ser Leu Val Ala Asn Thr Leu Gly Phe Ala Glu Met
            1285                1290                1295

Gly Pro Ile Lys Ser Leu Arg Thr Leu Arg Ala Leu Arg Pro Leu Arg
            1300                1305                1310

Ala Leu Ser Arg Phe Glu Gly Met Arg Val Val Val Asn Ala Leu Val
            1315                1320                1325

Gly Ala Ile Pro Ser Ile Met Asn Val Leu Leu Val Cys Leu Ile Phe
            1330                1335                1340

Trp Leu Ile Phe Ser Ile Met Gly Val Asn Leu Phe Ala Gly Lys Phe
1345                1350                1355                1360

Gly Arg Cys Ile Asn Gln Thr Glu Gly Asp Leu Pro Leu Asn Tyr Thr
            1365                1370                1375

Ile Val Asn Asn Lys Ser Gln Cys Glu Ser Leu Asn Leu Thr Gly Glu
            1380                1385                1390

Leu Tyr Trp Thr Lys Val Lys Val Asn Phe Asp Asn Val Gly Ala Gly
            1395                1400                1405

Tyr Leu Ala Leu Leu Gln Val Ala Thr Phe Lys Gly Trp Met Asp Ile
            1410                1415                1420

Met Tyr Ala Ala Val Asp Ser Arg Gly Tyr Glu Glu Gln Pro Gln Trp
1425                1430                1435                1440

Glu Tyr Asn Leu Tyr Met Tyr Ile Tyr Phe Val Ile Phe Ile Ile Phe
            1445                1450                1455

Gly Ser Phe Phe Thr Leu Asn Leu Phe Ile Gly Val Ile Ile Asp Asn
            1460                1465                1470

Phe Asn Gln Gln Lys Lys Lys Leu Gly Gly Gln Asp Ile Phe Met Thr
            1475                1480                1485

Glu Glu Gln Lys Lys Tyr Tyr Asn Ala Met Lys Lys Leu Gly Ser Lys
            1490                1495                1500

Lys Pro Gln Lys Pro Ile Pro Arg Pro Leu Asn Lys Tyr Gln Gly Phe
1505                1510                1515                1520

Ile Phe Asp Ile Val Thr Lys Gln Ala Phe Asp Val Thr Ile Met Phe
            1525                1530                1535

Leu Ile Cys Leu Asn Met Val Thr Met Met Val Glu Thr Asp Asp Gln
            1540                1545                1550

Ser Pro Glu Lys Ile Asn Ile Leu Ala Lys Ile Asn Leu Leu Phe Val
            1555                1560                1565

Ala Ile Phe Thr Gly Glu Cys Ile Val Lys Leu Ala Ala Leu Arg His
            1570                1575                1580

Tyr Tyr Phe Thr Asn Ser Trp Asn Ile Phe Asp Phe Val Val Val Ile
1585                1590                1595                1600

Leu Ser Ile Val Gly Thr Val Leu Ser Asp Ile Ile Gln Lys Tyr Phe
            1605                1610                1615

Phe Ser Pro Thr Leu Phe Arg Val Ile Arg Leu Ala Arg Ile Gly Arg
            1620                1625                1630

Ile Leu Arg Leu Ile Arg Gly Ala Lys Gly Ile Arg Thr Leu Leu Phe
            1635                1640                1645

Ala Leu Met Met Ser Leu Pro Ala Leu Phe Asn Ile Gly Leu Leu Leu
            1650                1655                1660
```

-continued

```
Phe Leu Val Met Phe Ile Tyr Ser Ile Phe Gly Met Ala Asn Phe Ala
1665                1670                1675                1680

Tyr Val Lys Trp Glu Ala Gly Ile Asp Asp Met Phe Asn Phe Gln Thr
                1685                1690                1695

Phe Ala Asn Ser Met Leu Cys Leu Phe Gln Ile Thr Thr Ser Ala Gly
            1700                1705                1710

Trp Asp Gly Leu Leu Ser Pro Ile Leu Asn Thr Gly Pro Pro Tyr Cys
        1715                1720                1725

Asp Pro Thr Leu Pro Asn Ser Asn Gly Ser Arg Gly Asp Cys Gly Ser
    1730                1735                1740

Pro Ala Val Gly Ile Leu Phe Phe Thr Thr Tyr Ile Ile Ile Ser Phe
1745                1750                1755                1760

Leu Ile Val Val Asn Met Tyr Ile Ala Ile Ile Leu Glu Asn Phe Ser
                1765                1770                1775

Val Ala Thr Glu Glu Ser Thr Glu Pro Leu Ser Glu Asp Asp Phe Asp
            1780                1785                1790

Met Phe Tyr Glu Ile Trp Glu Lys Phe Asp Pro Glu Ala Thr Gln Phe
        1795                1800                1805

Ile Glu Tyr Ser Val Leu Ser Asp Phe Ala Asp Ala Leu Ser Glu Pro
    1810                1815                1820

Leu Arg Ile Ala Lys Pro Asn Gln Ile Ser Leu Ile Asn Met Asp Leu
1825                1830                1835                1840

Pro Met Val Ser Gly Asp Arg Ile His Cys Met Asp Ile Leu Phe Ala
                1845                1850                1855

Phe Thr Lys Arg Val Leu Gly Glu Ser Gly Glu Met Asp Ala Leu Lys
            1860                1865                1870

Ile Gln Met Glu Glu Lys Phe Met Ala Ala Asn Pro Ser Lys Ile Ser
        1875                1880                1885

Tyr Glu Pro Ile Thr Thr Thr Leu Arg Arg Lys His Glu Glu Val Ser
    1890                1895                1900

Ala Met Val Ile Gln Arg Ala Phe Arg Arg His Leu Leu Gln Arg Ser
1905                1910                1915                1920

Leu Lys His Ala Ser Phe Leu Phe Arg Gln Gln Ala Gly Ser Gly Leu
                1925                1930                1935

Ser Glu Glu Asp Ala Pro Glu Arg Glu Gly Leu Ile Ala Tyr Val Met
            1940                1945                1950

Ser Glu Asn Phe Ser Arg Pro Leu Gly Pro Pro Ser Ser Ser Ser Ile
        1955                1960                1965

Ser Ser Thr Ser Phe Pro Pro Ser Tyr Asp Ser Val Thr Arg Ala Thr
    1970                1975                1980

Ser Asp Asn Leu Gln Val Arg Gly Ser Asp Tyr Ser His Ser Glu Asp
1985                1990                1995                2000

Leu Ala Asp Phe Pro Pro Ser Pro Asp Arg Asp Arg Glu Ser Ile Val
                2005                2010                2015
```